(12) United States Patent
Meyers

(10) Patent No.: US 7,160,693 B2
(45) Date of Patent: Jan. 9, 2007

(54) HUMAN HYDROLASE FAMILY MEMBERS AND USES THEREOF

(75) Inventor: Rachel E. Meyers, Newton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/244,219

(22) Filed: Oct. 5, 2005

(65) Prior Publication Data

US 2006/0035362 A1    Feb. 16, 2006

Related U.S. Application Data

(60) Division of application No. 10/193,452, filed on Jul. 11, 2002, now abandoned, which is a continuation-in-part of application No. 09/816,664, filed on Mar. 23, 2001, now abandoned.

(60) Provisional application No. 60/267,054, filed on Feb. 7, 2001, provisional application No. 60/238,170, filed on Oct. 5, 2000, provisional application No. 60/235,033, filed on Sep. 25, 2000, provisional application No. 60/226,774, filed on Aug. 21, 2000, provisional application No. 60/220,040, filed on Jul. 21, 2000, provisional application No. 60/220,008, filed on Jul. 21, 2000, provisional application No. 60/214,948, filed on Jun. 29, 2000, provisional application No. 60/213,688, filed on Jun. 23, 2000, provisional application No. 60/209,949, filed on Jun. 6, 2000, provisional application No. 60/206,036, filed on May 22, 2000, provisional application No. 60/205,442, filed on May 19, 2000, provisional application No. 60/199,559, filed on Apr. 25, 2000, provisional application No. 60/191,973, filed on Mar. 24, 2000.

(51) Int. Cl.
| | |
|---|---|
| C12Q 1/34 | (2006.01) |
| C12Q 1/68 | (2006.01) |
| C12N 1/20 | (2006.01) |
| C12N 15/00 | (2006.01) |
| C07H 21/04 | (2006.01) |

(52) U.S. Cl. .................. 435/18; 435/252.3; 435/320.1; 435/6; 536/23.2

(58) Field of Classification Search ............... 536/23.2; 435/252.3, 320.1, 6, 18
See application file for complete search history.

(56) References Cited

U.S. PATENT DOCUMENTS 6,569,662 B1 * 5/2003 Tang et al. ................. 435/212

FOREIGN PATENT DOCUMENTS

WO    WO 01/53312 A1    7/2001

* cited by examiner

Primary Examiner—Maryam Monshipouri
(74) Attorney, Agent, or Firm—Millennium Pharmaceuticals Inc.

(57) ABSTRACT

The invention provides isolated nucleic acids molecules, designated 26443 and 46873 nucleic acid molecules, which encode novel human hydrolase family members. The invention also provides antisense nucleic acid molecules, recombinant expression vectors containing 26443 and 46873 nucleic acid molecules, host cells into which the expression vectors have been introduced, and nonhuman transgenic animals in which a 26443 and 46873 gene has been introduced or disrupted. The invention still further provides isolated 26443 and 46873 proteins, fusion proteins, antigenic peptides and anti-26443 or 46873 antibodies. Diagnostic methods utilizing compositions of the invention are also provided.

12 Claims, 9 Drawing Sheets

```
┌START SEQ ID NO:1
▼
GCTGAAGCGGGGTAATTCCTCTCCTGCAATTACTTTTGGATGGAAGTATGCCCCTTTCTCAGTAGAAGATGGTAATCTT
                  ┌START SEQ ID NO:2
                  ▼
                  M   E   K   G   M   S   S   G   E   G   L   P   S   R   S   S   Q    17
GGAGAATGACC  ATG GAG AAG GGG ATG AGT TCT GGA GAA GGG CTG CCT TCC AGA TCA TCT CAG    51
            └START SEQ ID NO:3
   V   S   A   G   K   I   T   A   K   E   L   E   T   K   Q   S   Y   K   E   K     37
  GTT TCG GCT GGT AAA ATA ACA GCC AAA GAG TTG GAA ACA AAG CAG TCC TAT AAA GAG AAA   111

R   G   G   F   V   L   V   H   A   G   A   G   Y   H   S   E   S   K   A   K     57
  CGA GGA GGC TTT GTG TTG GTG CAT GCA GGT GCA GGT TAT CAT TCT GAA TCC AAA GCC AAG   171

E   Y   K   H   V   C   K   R   A   C   Q   K   A   I   E   K   L   Q   A   G     77
  GAG TAT AAA CAT GTA TGC AAA CGA GCT TGT CAG AAG GCA ATT GAA AAG CTG CAG GCC GGT   231

A   L   A   T   D   A   V   T   A   A   L   V   E   L   E   D   S   P   F   T     97
  GCT CTT GCA ACT GAC GCA GTC ACT GCA GCA CTG GTG GAA CTT GAG GAT TCT CCT TTT ACA   291

N   A   G   M   G   S   N   L   N   L   L   G   E   I   E   C   D   A   S   I    117
  AAT GCA GGA ATG GGA TCT AAT CTA AAT CTG TTA GGT GAA ATT GAG TGT GAT GCC AGC ATA   351

M   D   G   K   S   L   N   F   G   A   V   G   A   L   S   G   I   K   N   P    137
  ATG GAT GGA AAA TCC TTA AAT TTT GGA GCA GTT GGA GCA CTG AGT GGA ATC AAG AAC CCA   411

V   S   V   A   N   R   L   L   C   E   G   Q   K   G   K   L   S   A   G   R    157
  GTC TCG GTT GCC AAC AGA CTC TTA TGT GAA GGG CAG AAG GGC AAG CTC TCG GCT GGC AGA   471

I   P   P   C   F   L   V   G   E   G   A   Y   R   W   A   V   D   H   G   I    177
  ATT CCT CCC TGC TTT TTA GTT GGA GAA GGA GCC TAC AGA TGG GCA GTA GAT CAT GGA ATA   531

P   S   C   P   P   N   I   M   T   T   R   F   S   L   A   A   F   K   R   N    197
  CCC TCT TGC CCT CCT AAC ATC ATG ACC ACA AGA TTC AGT TTA GCT GCA TTT AAA AGA AAC   591

K   R   K   L   E   L   A   E   R   V   D   T   D   F   M   Q   L   K   K   R    217
  AAG AGG AAA CTA GAG CTG GCA GAA AGG GTG GAC ACA GAT TTT ATG CAA CTA AAG AAA AGA   651

R   Q   S   S   E   K   E   N   D   S   G   T   L   D   T   V   G   A   V   V    237
  AGA CAA TCA AGT GAG AAG GAA AAT GAC TCA GGC ACT TTG GAC ACG GTA GGC GCT GTG GTT   711
```

Fig. 1A

```
  V   D   H   E   G   N   V   A   A   A   V   S   S   G   G   L   A   L   K   H   257
GTG GAC CAC GAA GGG AAT GTT GCT GCT GCT GTC TCC AGT GGA GGC TTG GCC TTG AAA CAT  771

P   G   R   V   G   Q   A   A   L   Y   G   C   G   C   W   E   N   T   G       277
CCG GGG AGA GTT GGG CAG GCT GCT CTT TAT GGA TGT GGC TGC TGG GCT GAA AAT ACT GGA  831

A   H   N   P   Y   S   T   A   V   S   T   S   G   C   G   E   H   L   V   R   297
GCT CAT AAC CCC TAC TCC ACA GCT GTG AGT ACC TCA GGA TGT GGA GAG CAT CTT GTG CGC  891

T   I   L   A   R   E   C   S   H   A   L   Q   A   E   D   A   H   Q   A   L   317
ACC ATA CTG GCT AGA GAA TGT TCA CAT GCT TTA CAA GCT GAG GAT GCT CAC CAA GCC CTG  951

L   E   T   M   Q   N   K   F   I   S   S   P   F   L   A   S   E   D   G   V   337
TTG GAG ACT ATG CAA AAC AAG TTT ATC AGT TCA CCT TTC CTT GCC AGT GAA GAT GGC GTG 1011

L   G   G   V   I   V   L   R   S   C   R   C   S   A   E   P   D   S   S   Q   357
CTT GGC GGA GTG ATT GTC CTC CGT TCA TGC AGA TGT TCT GCC GAG CCT GAC TCC TCC CAA 1071

N   K   Q   T   L   L   V   E   F   L   W   S   H   T   T   E   S   M   C   V   377
AAT AAG CAG ACA CTT CTA GTG GAA TTT CTG TGG AGC CAC ACG ACG GAG AGC ATG TGT GTC 1131

G   Y   M   S   A   Q   D   G   K   A   K   T   H   I   S   R   L   P   P   G   397
GGA TAT ATG TCA GCC CAG GAT GGG AAA GCC AAG ACT CAC ATT TCA AGA CTT CCT CCT GGT 1191

A   V   A   G   Q   S   V   A   I   E   G   G   V   C   R   L   E   S   P   V   417
GCG GTG GCA GGA CAG TCT GTG GCA ATC GAA GGT GGG GTG TGC CGC CTG GAG AGC CCA GTG 1251
              ┌ END SEQ ID NO:2
            N │  * ┌ END SEQ ID NO:3                                              419
           AAC TGA                                                               1257
```

CCCTTCAGGCTGAGTGTGAAGCGTCTCAGAGGCATTTCAGAACCTGAGCTTTTGGGGGTTTTTAACTGAAGTTGGTTGT
TTTATCTTTCTTGTTTTATAATTCCTATTGCAACCTCGTGCACTGCTCGAGACACAAGTGCTGCTGTAGTTAGCGCTTA
GTGACACGCGGGCCTTTGGTGGGTGAGCGGGACTGTGTGTGAGTGTGTGCGCGTATGTGCGCACATATGTGTATGTGTG
GAGTATGTGTGTTTGCTTCTCCGTGGATGAAATAGAAACTCCTCATTGTGTGACCAGGAATGGTTAAATCATCTTTACA
AAATGTGTGCTTTAACTGTTTACAAGTAAAACCTAAAGTTGCAGGAAACATTTTTTATTTCGTAAAGAGGTACCAACTG
TCGCTGATGTGATATGTCAGAACTGAAGAGTAAATCTACTTGTTTAAAATGACTTGACAGTGGTAGTGCTCCATTTAATA
ACAGTAATAAGTAATAAAGTGTTTTTATTTGTTAACCAAAAAAAAAAAAAAAAAAAAAGGGCGGCCGCT
                                                              └ END SEQ ID NO:1

Fig. 1B

```
Alignments of top-scoring domains:
Asparaginase_2: domain 1 of 1, from 38 to 345: score 77.2, E = 3.4e-19
                *->gtlllaihgleGagdidssePKttnlPlvlttwrsealkhaveaawk
                     +  + h   Gag  + s    +   +        k a + a++
        26443  38 RGGFVLVHA--GAGYHSES-----KAKEYKHVC----KRACQKAIE  72 aLkaGgsALDaVekGvrllEnePcdfnaGyGgvldedGtveLDAsiMDGn
                 L aG  A DaV+ ++ +lE+ P  +naG G+ l  +G+ e DAsiMDG+
        26443  73 KLQAGALATDAVTAALVELEDSP-FTNAGMGSNLNLLGEIECDASIMDGK 121 tsssmvvieniFCRDGmkvGAVaglsrIkNPIsvARlVM..........e
                             +++GAV+ ls IkNP+svA  ++ ++++++ + +
        26443 122 S--------------LNFGAVGALSGIKNPVSVANRLLcegqkgklsaG  156 kTpHilLvgegAeeFAksqGfetedlstfetqewieewlaakeqkNywkr
                 p  +LvgegA   A  +G   ++ +  t    + +  k++        r
        26443 157 RIPPCFLVGEGAYRWAVDHGIPSCPPNIMTTRFSLAAFKRNKRKLELAER 206 vilDpSvycGPYktpgllkserdiPldnedseaGYLvddrqhgTIGmVAl
                v  D+ +      k  +     ++++      d    +T+G+V++
        26443 207 VDTDFMQL---------KKRRQSS---EKEN------DSGTLDTVGAVVV 238

DaeGnLAAaTSTgGmvnKmhGRVGDSPiiGAGaYAnnfaG......AvsA
                D eGn AAa S+gG+++K +GRVG  ++ G G+ A n++++++ ++Avs
        26443 239 DHEGNVAAAVSSGGLALKHPGRVGQAALYGCGCWAENTGAhmpystAVST 288

TGkGEviIRalpaydvValMeyGgkPlslaeaaakrItkalPkrGKnLKD
                 G GE + R+++a+            + +a  +  + ++
        26443 289 SGCGEHLVRTILARECSHALQAED----AHQALLETMQNKFIS------- 327 gsgGlIAlnhkGeiaapcnttgmfraahtAtedgttleYseigiwek<-*
                                      + f    A+edg   ++  i +
        26443 328 --------------------SPF----LASEDG---VLGG-VIVLR    345
```

```
                    ┌─ START SEQ ID NO:4
TCCGAGAGCGGTGGCGGGCTGAGCCGGTTACGAGCCGGCGTCGGGGAGCGGCGGTACCGGGCGGCTGCGGGGCTGGCTCG
                                                 START SEQ ID NO:5 ─┐  M   N   P   I   V   V    6
ACCCAGCTTGAGGTCTCGGCGTCCGCGTCCTGCGGTGCCCTGGGATCCGCCGAC ATG AAT CCC ATC GTA GTG   18
                                                START SEQ ID NO:6 ─┘
  V   H   G   G   G   A   G   P   I   S   K   D   R   K   E   R   V   H   Q   G   26
 GTC CAC GGC GGC GGA GCC GGT CCC ATC TCC AAG GAT CGG AAG GAG CGA GTG CAC CAG GGC   78

M   V   R   A   A   T   V   G   Y   G   I   L   R   E   G   G   S   A   V   D   46
 ATG GTC AGA GCC GCC ACC GTG GGC TAC GGC ATC CTC CGG GAG GGC GGG AGC GCC GTG GAT  138

A   V   E   G   A   V   V   A   L   E   D   D   P   E   F   N   A   G   C   G   66
 GCC GTA GAG GGA GCT GTC GTC GCC CTG GAA GAC GAT CCC GAG TTC AAC GCA GGT TGT GGG  198

S   V   L   N   T   N   G   E   V   E   M   D   A   S   I   M   D   G   K   D   86
 TCT GTC TTG AAC ACA AAT GGT GAG GTT GAA ATG GAT GCT AGT ATC ATG GAT GGA AAA GAC  258

L   S   A   G   A   V   S   A   V   Q   C   I   A   N   P   I   K   L   A   R  106
 CTG TCT GCA GGA GCA GTG TCC GCA GTC CAG TGT ATA GCA AAT CCC ATT AAA CTT GCT CGG  318

L   V   M   E   K   T   P   H   C   F   L   T   D   Q   G   A   A   Q   F   A  126
 CTT GTC ATG GAA AAG ACA CCT CAT TGC TTT CTG ACT GAC CAA GGC GCA GCG CAG TTT GCA  378

A   A   M   G   V   P   E   I   P   G   E   K   L   V   T   E   R   N   K   K  146
 GCA GCT ATG GGG GTT CCA GAG ATT CCT GGA GAA AAA CTG GTG ACA GAG AGA AAC AAA AAG  438

R   L   E   K   E   K   H   E   K   G   A   Q   K   T   D   C   Q   K   N   L  166
 CGC CTG GAA AAA GAG AAG CAT GAA AAA GGT GCT CAG AAA ACA GAT TGT CAA AAA AAC TTG  498

G   T   V   G   A   V   A   L   D   C   K   G   N   V   A   Y   A   T   S   T  186
 GGA ACC GTG GGT GCT GTT GCC TTG GAC TGC AAA GGG AAT GTA GCC TAC GCA ACC TCC ACA  558

G   G   I   V   N   K   M   V   G   R   V   G   D   S   P   C   L   G   A   G  206
 GGC GGT ATC GTT AAT AAA ATG GTC GGC CGC GTT GGG GAC TCA CCG TGT CTA GGA GCT GGA  618

G   Y   A   D   N   D   I   G   A   V   S   T   T   G   H   G   E   S   I   L  226
 GGT TAT GCC GAC AAT GAC ATC GGA GCC GTC TCA ACC ACA GGG CAT GGG GAA AGC ATC CTG  678

K   V   N   L   A   R   L   T   L   F   H   I   E   Q   G   K   T   V   E   E  246
 AAG GTG AAC CTG GCT AGA CTC ACC CTG TTC CAC ATA GAA CAA GGA AAG ACG GTA GAA GAG  738

A   A   D   L   S   L   G   Y   M   K   S   R   V   K   G   L   G   G   L   I  266
 GCT GCG GAC CTA TCG TTG GGT TAT ATG AAG TCA AGG GTT AAA GGT TTA GGT GGC CTC ATC  798

V   V   S   K   T   G   D   W   V   A   K   W   T   S   T   S   M   P   W   A  286
 GTG GTT AGC AAA ACA GGA GAC TGG GTG GCA AAG TGG ACC TCC ACC TCC ATG CCC TGG GCA  858

A   A   K   D   G   K   L   H   F   G   I   D   P   D   D   T   T   I   T   D  306
 GCC GCC AAG GAC GGC AAG CTG CAC TTC GGA ATT GAT CCT GAC GAT ACT ACT ATC ACC GAC  918
                    ┌─ END SEQ ID NO:5
  L   P   *        ┌─ END SEQ ID NO:6
 CTT CCC TAA

GCCGCTGGAAGATTGTATTCCAGATGCTAGCTTAGAGGTCAAGTACAGTCTCCTCATGAGACATAGCCTAATCAATTAG
ATCTAGAATTGGAAAAATTGTCCCGTCTGTCACTTGTTTTGTTGCCTTAATAAGCATCTGAATGTTTGGTTGTGGGGCG
GGTTCTGAAGCGATGAGAGAAATGCCCGTATTAGGAGGATTACTTGAGCCCTGGAGGTCAAAGCTGAGGTGAGCCATGA
TTACTCCACTGCACTCCAGCCTGGGCAACAGAGCCAGGCCCTGTATCAAAAAAAAAAAAAA ◄── END SEQ ID NO:4
```

```
Alignments of top-scoring domains:
Asparaginase_2: domain 1 of 1, from 1 to 302: score 252.3, E = 6.4e-72
                  *->gtlllIaihgleGagdidssePKttnlPlvlttwrsealkhaveaawk
                     + + +   hg Gag i+ +            ++ + +   a   ++
        46873    1    MNPIVVVHG-GGAGPISKD--------RKKERVHQ--GMVRAATVGYG  36 aLkaGgsALDaVekGvrllEnePcdfnaGyGgvldedGtveLDAsiMDGn
                  L   GgsA DaVe +v  lE++P +fnaG G+vl   +G+ve+DAsiMDG+
        46873   37    ILREGGSAVDAVEGAVVALEDDP-EFNAGCGSVLNTNGEVEMDASIMDGK  85 tsssmvvieniFCRDGmkvGAVaglsrIkNPIsvARlVMekTpHillvge
                          +  +GAV+ ++ I NPI +ARlVMekTpH +L  +
        46873   86    D--------------LSAGAVSAVQCIANPIKLARLVMEKTPHCFLTDQ 120 gAeeFAksqGfetedlstfetqewieewlaakeqkNywkrvilDpSvycG
                  gA +FA ++G+ + + +   t+ + +++  ++k  +k              ++
        46873  121    GAAQFAAAMGVPEIPGEKLVTERNKKRLEKEKHEK-----------GA--- 157

PYktpgllkserdiPldnedseaGYLvddrqhgTIGmVAlDaeGnLAAaT
                                ++   d++  +          gT+G+VAlD  Gn A  aT
        46873  158    -----------QKT--DCQKN----------LGTVGAVALDCKGNVAYAT 184

STgGmvnKmhGRVGDSPiiGAGaYAnnfaGAvsATGkGEviIRalpaydv
                  STgG+vnKm+GRVGDSP  GAG YA+n +GAVs TG+GE i    +a++
        46873  185    STGGIVNKMVGRVGDSPCLGAGGYADNDIGAVSTTGHGESILKVNLARLT 234

ValMeyGgkPlslaeaaakrI..tkalPkrGKnLKDgsgGlIAlnhkGei
                   e+G  +    eaa+ + + +k+  k          g gGlI ++++G
        46873  235    LFHIEQGK--T-VEEAADLSLgyMKSRVK-------GLGGLIVVSKTGDW 274 aapcnttgmfraahtAtedgttleYseigiwek<-*
                  a  + t+m  + A dg+     +++ ++
        46873  275    VAKWTSTSMP--W-AAAKDGKLHFGIDPD--DT     302
```

Fig. 8

SEQUENCE LISTING

```
<160> NUMBER OF SEQ ID NOS: 9

<210> SEQ ID NO 1
<211> LENGTH: 1888
<212> TYPE: DNA
<213> ORGANISM: Homo sapiens
<220> FEATURE:
<221> NAME/KEY: CDS
<222> LOCATION: (91)...(1344)

<400> SEQUENCE: 1
gctgaagcgg ggtaattcct ctcctgcaat tactttgga tggaagtatg cccctttctc      60
agtagaagat ggtaatcttg gagaatgacc atg gag aag ggg atg agt tct gga     114
                                 Met Glu Lys Gly Met Ser Ser Gly
```

-continued

|  | 1 |  | 5 |  |  |
|---|---|---|---|---|---|
| gaa ggg ctg cct tcc aga tca tct cag gtt tcg gct ggt aaa ata aca | | | | | 162 |
| Glu Gly Leu Pro Ser Arg Ser Ser Gln Val Ser Ala Gly Lys Ile Thr | | | | | |
| 10 | | 15 | | 20 | |
| gcc aaa gag ttg gaa aca aag cag tcc tat aaa gag aaa cga gga ggc | | | | | 210 |
| Ala Lys Glu Leu Glu Thr Lys Gln Ser Tyr Lys Glu Lys Arg Gly Gly | | | | | |
| 25 | | 30 | | 35 | 40 |
| ttt gtg ttg gtg cat gca ggt gca ggt tat cat tct gaa tcc aaa gcc | | | | | 258 |
| Phe Val Leu Val His Ala Gly Ala Gly Tyr His Ser Glu Ser Lys Ala | | | | | |
| | | 45 | | 50 | 55 |
| aag gag tat aaa cat gta tgc aaa cga gct tgt cag aag gca att gaa | | | | | 306 |
| Lys Glu Tyr Lys His Val Cys Lys Arg Ala Cys Gln Lys Ala Ile Glu | | | | | |
| | 60 | | 65 | | 70 |
| aag ctg cag gcc ggt gct ctt gca act gac gca gtc act gca gca ctg | | | | | 354 |
| Lys Leu Gln Ala Gly Ala Leu Ala Thr Asp Ala Val Thr Ala Ala Leu | | | | | |
| | 75 | | 80 | | 85 |
| gtg gaa ctt gag gat tct cct ttt aca aat gca gga atg gga tct aat | | | | | 402 |
| Val Glu Leu Glu Asp Ser Pro Phe Thr Asn Ala Gly Met Gly Ser Asn | | | | | |
| | 90 | | 95 | | 100 |
| cta aat ctg tta ggt gaa att gag tgt gat gcc agc ata atg gat gga | | | | | 450 |
| Leu Asn Leu Leu Gly Glu Ile Glu Cys Asp Ala Ser Ile Met Asp Gly | | | | | |
| 105 | | 110 | | 115 | 120 |
| aaa tcc tta aat ttt gga gca gtt gga gca ctg agt gga atc aag aac | | | | | 498 |
| Lys Ser Leu Asn Phe Gly Ala Val Gly Ala Leu Ser Gly Ile Lys Asn | | | | | |
| | | 125 | | 130 | 135 |
| cca gtc tcg gtt gcc aac aga ctc tta tgt gaa ggg cag aag ggc aag | | | | | 546 |
| Pro Val Ser Val Ala Asn Arg Leu Leu Cys Glu Gly Gln Lys Gly Lys | | | | | |
| | | 140 | | 145 | 150 |
| ctc tcg gct ggc aga att cct ccc tgc ttt tta gtt gga gaa gga gcc | | | | | 594 |
| Leu Ser Ala Gly Arg Ile Pro Pro Cys Phe Leu Val Gly Glu Gly Ala | | | | | |
| | 155 | | 160 | | 165 |
| tac aga tgg gca gta gat cat gga ata ccc tct tgc cct cct aac atc | | | | | 642 |
| Tyr Arg Trp Ala Val Asp His Gly Ile Pro Ser Cys Pro Pro Asn Ile | | | | | |
| | 170 | | 175 | | 180 |
| atg acc aca aga ttc agt tta gct gca ttt aaa aga aac aag agg aaa | | | | | 690 |
| Met Thr Thr Arg Phe Ser Leu Ala Ala Phe Lys Arg Asn Lys Arg Lys | | | | | |
| 185 | | 190 | | 195 | 200 |
| cta gag ctg gca gaa agg gtg gac aca gat ttt atg caa cta aag aaa | | | | | 738 |
| Leu Glu Leu Ala Glu Arg Val Asp Thr Asp Phe Met Gln Leu Lys Lys | | | | | |
| | | 205 | | 210 | 215 |
| aga aga caa tca agt gag aag gaa aat gac tca ggc act ttg gac acg | | | | | 786 |
| Arg Arg Gln Ser Ser Glu Lys Glu Asn Asp Ser Gly Thr Leu Asp Thr | | | | | |
| | | 220 | | 225 | 230 |
| gta ggc gct gtg gtt gtg gac cac gaa ggg aat gtt gct gct gct gtc | | | | | 834 |
| Val Gly Ala Val Val Val Asp His Glu Gly Asn Val Ala Ala Ala Val | | | | | |
| | 235 | | 240 | | 245 |
| tcc agt gga ggc ttg gcc ttg aaa cat ccg ggg aga gtt ggg cag gct | | | | | 882 |
| Ser Ser Gly Gly Leu Ala Leu Lys His Pro Gly Arg Val Gly Gln Ala | | | | | |
| | 250 | | 255 | | 260 |
| gct ctt tat gga tgt ggc tgc tgg gct gaa aat act gga gct cat aac | | | | | 930 |
| Ala Leu Tyr Gly Cys Gly Cys Trp Ala Glu Asn Thr Gly Ala His Asn | | | | | |
| 265 | | 270 | | 275 | 280 |
| ccc tac tcc aca gct gtg agt acc tca gga tgt gga gag cat ctt gtg | | | | | 978 |
| Pro Tyr Ser Thr Ala Val Ser Thr Ser Gly Cys Gly Glu His Leu Val | | | | | |
| | | 285 | | 290 | 295 |
| cgc acc ata ctg gct aga gaa tgt tca cat gct tta caa gct gag gat | | | | | 1026 |
| Arg Thr Ile Leu Ala Arg Glu Cys Ser His Ala Leu Gln Ala Glu Asp | | | | | |
| | 300 | | 305 | | 310 |
| gct cac caa gcc ctg ttg gag act atg caa aac aag ttt atc agt tca | | | | | 1074 |

-continued

```
Ala His Gln Ala Leu Leu Glu Thr Met Gln Asn Lys Phe Ile Ser Ser
        315                 320                 325 cct ttc ctt gcc agt gaa gat ggc gtg ctt ggc gga gtg att gtc ctc      1122
Pro Phe Leu Ala Ser Glu Asp Gly Val Leu Gly Gly Val Ile Val Leu
        330                 335                 340 cgt tca tgc aga tgt tct gcc gag cct gac tcc tcc caa aat aag cag      1170
Arg Ser Cys Arg Cys Ser Ala Glu Pro Asp Ser Ser Gln Asn Lys Gln
345                 350                 355                 360 aca ctt cta gtg gaa ttt ctg tgg agc cac acg acg gag agc atg tgt      1218
Thr Leu Leu Val Glu Phe Leu Trp Ser His Thr Thr Glu Ser Met Cys
                365                 370                 375 gtc gga tat atg tca gcc cag gat ggg aaa gcc aag act cac att tca      1266
Val Gly Tyr Met Ser Ala Gln Asp Gly Lys Ala Lys Thr His Ile Ser
        380                 385                 390 aga ctt cct cct ggt gcg gtg gca gga cag tct gtg gca atc gaa ggt      1314
Arg Leu Pro Pro Gly Ala Val Ala Gly Gln Ser Val Ala Ile Glu Gly
        395                 400                 405 ggg gtg tgc cgc ctg gag agc cca gtg aac tgacccttca ggctgagtgt        1364
Gly Val Cys Arg Leu Glu Ser Pro Val Asn
        410                 415 gaagcgtctc agaggcattt cagaacctga gcttttgggg gttttaact gaagttggtt     1424 gttttatctt tcttgtttta taattcctat gcaacctcg tgcactgctc gagacacaag    1484
tgctgctgta gttagcgctt agtgacacgc gggcctttgg tgggtgagcg ggactgtgtg   1544
tgagtgtgtg cgcgtatgtg cgcacatatg tgtatgtgtg gagtatgtgt gtttgcttct   1604
ccgtggatga aatagaaact cctcattgtg tgaccaggaa tggttaaatc atctttacaa   1664
aatgtgtgct ttaactgttt acaagtaaaa cctaaagttg caggaaacat tttttatttc   1724
gtaaagaggt accaactgtc gctgatgtga tatgtcagaa ctgaagagta aatctacttg   1784
tttaaatgac ttgacagtgg tagtgctcca tttaataaca gtaataagta ataaagtgtt   1844
tttatttgtt aaccaaaaaa aaaaaaaaaa aaagggcggc cgct                    1888
```

<210> SEQ ID NO 2
<211> LENGTH: 418
<212> TYPE: PRT
<213> ORGANISM: Homo sapiens

<400> SEQUENCE: 2

```
Met Glu Lys Gly Met Ser Ser Gly Glu Gly Leu Pro Ser Arg Ser Ser
1               5                   10                  15

Gln Val Ser Ala Gly Lys Ile Thr Ala Lys Glu Leu Glu Thr Lys Gln
            20                  25                  30

Ser Tyr Lys Glu Lys Arg Gly Gly Phe Val Leu Val His Ala Gly Ala
        35                  40                  45

Gly Tyr His Ser Glu Ser Lys Ala Lys Glu Tyr Lys His Val Cys Lys
    50                  55                  60

Arg Ala Cys Gln Lys Ala Ile Glu Lys Leu Gln Ala Gly Ala Leu Ala
65              70                  75                  80

Thr Asp Ala Val Thr Ala Ala Leu Val Glu Leu Glu Asp Ser Pro Phe
            85                  90                  95

Thr Asn Ala Gly Met Gly Ser Asn Leu Asn Leu Gly Glu Ile Glu
            100                 105                 110

Cys Asp Ala Ser Ile Met Asp Gly Lys Ser Leu Asn Phe Gly Ala Val
        115                 120                 125

Gly Ala Leu Ser Gly Ile Lys Asn Pro Val Ser Val Ala Asn Arg Leu
    130                 135                 140
```

-continued

```
Leu Cys Glu Gly Gln Lys Gly Lys Leu Ser Ala Gly Arg Ile Pro Pro
145                 150                 155                 160

Cys Phe Leu Val Gly Glu Gly Ala Tyr Arg Trp Ala Val Asp His Gly
                165                 170                 175

Ile Pro Ser Cys Pro Pro Asn Ile Met Thr Thr Arg Phe Ser Leu Ala
            180                 185                 190

Ala Phe Lys Arg Asn Lys Arg Leu Glu Leu Ala Glu Arg Val Asp
        195                 200                 205

Thr Asp Phe Met Gln Leu Lys Lys Arg Arg Gln Ser Ser Glu Lys Glu
210                 215                 220

Asn Asp Ser Gly Thr Leu Asp Thr Val Gly Ala Val Val Asp His
225                 230                 235                 240

Glu Gly Asn Val Ala Ala Val Ser Ser Gly Gly Leu Ala Leu Lys
                245                 250                 255

His Pro Gly Arg Val Gly Gln Ala Ala Leu Tyr Gly Cys Gly Cys Trp
            260                 265                 270

Ala Glu Asn Thr Gly Ala His Asn Pro Tyr Ser Thr Ala Val Ser Thr
        275                 280                 285

Ser Gly Cys Gly Glu His Leu Val Arg Thr Ile Leu Ala Arg Glu Cys
290                 295                 300

Ser His Ala Leu Gln Ala Glu Asp Ala His Gln Ala Leu Leu Glu Thr
305                 310                 315                 320

Met Gln Asn Lys Phe Ile Ser Ser Pro Phe Leu Ala Ser Glu Asp Gly
                325                 330                 335

Val Leu Gly Gly Val Ile Val Leu Arg Ser Cys Arg Cys Ser Ala Glu
            340                 345                 350

Pro Asp Ser Ser Gln Asn Lys Gln Thr Leu Leu Val Glu Phe Leu Trp
        355                 360                 365

Ser His Thr Thr Glu Ser Met Cys Val Gly Tyr Met Ser Ala Gln Asp
370                 375                 380

Gly Lys Ala Lys Thr His Ile Ser Arg Leu Pro Pro Gly Ala Val Ala
385                 390                 395                 400

Gly Gln Ser Val Ala Ile Glu Gly Gly Val Cys Arg Leu Glu Ser Pro
                405                 410                 415

Val Asn
```

<210> SEQ ID NO 3
<211> LENGTH: 1257
<212> TYPE: DNA
<213> ORGANISM: Homo sapiens

<400> SEQUENCE: 3

```
atggagaagg ggatgagttc tggagaaggg ctgccttcca gatcatctca ggtttcggct      60
ggtaaaataa cagccaaaga gttggaaaca aagcagtcct ataaagaaa acgaggaggc     120
tttgtgttgg tgcatgcagg tgcaggttat cattctgaat ccaaagccaa ggagtataaa     180
catgtatgca aacgagcttg tcagaaggca attgaaaagc tgcaggccgg tgctcttgca     240
actgacgcag tcactgcagc actggtggaa cttgaggatt ctccttttac aaatgcagga     300
atgggatcta atctaaatct gttaggtgaa attgagtgtg atgccagcat aatggatgga     360
aaatccttaa attttggagc agttggagca ctgagtggaa tcaagaaccc agtctcggtt     420
gccaacagac tcttatgtga agggcagaag ggcaagctct cggctggcag aattcctccc     480
tgcttttttag ttggagaagg agcctacaga tgggcagtag atcatggaat accctcttgc     540
```

-continued

```
cctcctaaca tcatgaccac aagattcagt ttagctgcat ttaaaagaaa caagaggaaa      600
ctagagctgg cagaaagggt ggacacagat tttatgcaac taaagaaaag aagacaatca      660
agtgagaagg aaaatgactc aggcactttg gacacggtag cgctgtggt tgtggaccac       720 gaagggaatg ttgctgctgc tgtctccagt ggaggcttgg ccttgaaaca tccggggaga      780
gttgggcagg ctgctctttta tggatgtggc tgctgggctg aaaatactgg agctcataac    840
ccctactcca cagctgtgag tacctcagga tgtggagagc atcttgtgcg caccatactg     900
gctagagaat gttcacatgc tttacaagct gaggatgctc accaagccct gttggagact     960
atgcaaaaca agtttatcag ttcaccttc cttgccagtg aagatggcgt gcttggcgga     1020
gtgattgtcc tccgttcatg cagatgttct gccgagcctg actcctccca aaataagcag    1080
acacttctag tggaatttct gtggagccac acgacggaga gcatgtgtgt cggatatatg    1140
tcagcccagg atgggaaagc caagactcac atttcaagac ttcctcctgg tgcggtggca    1200
ggacagtctg tggcaatcga aggtggggtg tgccgcctgg agagcccagt gaactga       1257
```

<210> SEQ ID NO 4
<211> LENGTH: 1358
<212> TYPE: DNA
<213> ORGANISM: Homo sapiens
<220> FEATURE:
<221> NAME/KEY: CDS
<222> LOCATION: (134)...(1057)

<400> SEQUENCE: 4

```
tccgagagcg gtggcgggct gagcggttac gagccggcgt cggggagcgg cggtaccggg       60
cggctgcggg gctggctcga cccagcttga ggtctcggcg tccgcgtcct gcggtgccct      120
gggatccgcc gac atg aat ccc atc gta gtg gtc cac ggc ggc gga gcc         169
            Met Asn Pro Ile Val Val Val His Gly Gly Gly Ala
              1               5                  10 ggt ccc atc tcc aag gat cgg aag gag cga gtg cac cag ggc atg gtc         217
Gly Pro Ile Ser Lys Asp Arg Lys Glu Arg Val His Gln Gly Met Val
         15                  20                  25 aga gcc gcc acc gtg ggc tac ggc atc ctc cgg gag ggc ggg agc gcc         265
Arg Ala Ala Thr Val Gly Tyr Gly Ile Leu Arg Glu Gly Gly Ser Ala
 30                  35                  40 gtg gat gcc gta gag gga gct gtc gtc gcc ctg gaa gac gat ccc gag         313
Val Asp Ala Val Glu Gly Ala Val Val Ala Leu Glu Asp Asp Pro Glu
     45                  50                  55                  60 ttc aac gca ggt tgt ggg tct gtc ttg aac aca aat ggt gag gtt gaa         361
Phe Asn Ala Gly Cys Gly Ser Val Leu Asn Thr Asn Gly Glu Val Glu
                 65                  70                  75 atg gat gct agt atc atg gat gga aaa gac ctg tct gca gga gca gtg         409
Met Asp Ala Ser Ile Met Asp Gly Lys Asp Leu Ser Ala Gly Ala Val
             80                  85                  90 tcc gca gtc cag tgt ata gca aat ccc att aaa ctt gct cgg ctt gtc         457
Ser Ala Val Gln Cys Ile Ala Asn Pro Ile Lys Leu Ala Arg Leu Val
         95                 100                 105 atg gaa aag aca cct cat tgc ttt ctg act gac caa ggc gca gcg cag         505
Met Glu Lys Thr Pro His Cys Phe Leu Thr Asp Gln Gly Ala Ala Gln
 110                 115                 120 ttt gca gca gct atg ggg gtt cca gag att cct gga gaa aaa ctg gtg         553
Phe Ala Ala Ala Met Gly Val Pro Glu Ile Pro Gly Glu Lys Leu Val
     125                 130                 135                 140 aca gag aga aac aaa aag cgc ctg gaa aaa gag aag cat gaa aaa ggt         601
Thr Glu Arg Asn Lys Lys Arg Leu Glu Lys Glu Lys His Glu Lys Gly
                145                 150                 155
```

```
gct cag aaa aca gat tgt caa aaa aac ttg gga acc gtg ggt gct gtt       649
Ala Gln Lys Thr Asp Cys Gln Lys Asn Leu Gly Thr Val Gly Ala Val
            160                 165                 170 gcc ttg gac tgc aaa ggg aat gta gcc tac gca acc tcc aca ggc ggt       697
Ala Leu Asp Cys Lys Gly Asn Val Ala Tyr Ala Thr Ser Thr Gly Gly
        175                 180                 185 atc gtt aat aaa atg gtc ggc cgc gtt ggg gac tca ccg tgt cta gga       745
Ile Val Asn Lys Met Val Gly Arg Val Gly Asp Ser Pro Cys Leu Gly
    190                 195                 200 gct gga ggt tat gcc gac aat gac atc gga gcc gtc tca acc aca ggg       793
Ala Gly Gly Tyr Ala Asp Asn Asp Ile Gly Ala Val Ser Thr Thr Gly
205                 210                 215                 220 cat ggg gaa agc atc ctg aag gtg aac ctg gct aga ctc acc ctg ttc       841
His Gly Glu Ser Ile Leu Lys Val Asn Leu Ala Arg Leu Thr Leu Phe
                225                 230                 235 cac ata gaa caa gga aag acg gta gaa gag gct gcg gac cta tcg ttg       889
His Ile Glu Gln Gly Lys Thr Val Glu Glu Ala Ala Asp Leu Ser Leu
            240                 245                 250 ggt tat atg aag tca agg gtt aaa ggt tta ggt ggc ctc atc gtg gtt       937
Gly Tyr Met Lys Ser Arg Val Lys Gly Leu Gly Gly Leu Ile Val Val
        255                 260                 265 agc aaa aca gga gac tgg gtg gca aag tgg acc tcc acc tcc atg ccc       985
Ser Lys Thr Gly Asp Trp Val Ala Lys Trp Thr Ser Thr Ser Met Pro
    270                 275                 280 tgg gca gcc gcc aag gac ggc aag ctg cac ttc gga att gat cct gac      1033
Trp Ala Ala Ala Lys Asp Gly Lys Leu His Phe Gly Ile Asp Pro Asp
285                 290                 295                 300 gat act act atc acc gac ctt ccc taagccgctg gaagattgta ttccagatgc     1087
Asp Thr Thr Ile Thr Asp Leu Pro
                305 tagcttagag gtcaagtaca gtctcctcat gagacatagc ctaatcaatt agatctagaa    1147 ttggaaaaat tgtcccgtct gtcacttgtt ttgttgcctt aataagcatc tgaatgtttg    1207 gttgtggggc gggttctgaa gcgatgagag aaatgcccgt attaggagga ttacttgagc    1267 cctggaggtc aaagctgagg tgagccatga ttactccact gcactccagc ctgggcaaca    1327 gagccaggcc ctgtatcaaa aaaaaaaaaa a                                   1358

<210> SEQ ID NO 5
<211> LENGTH: 308
<212> TYPE: PRT
<213> ORGANISM: Homo sapiens

<400> SEQUENCE: 5

Met Asn Pro Ile Val Val His Gly Gly Ala Gly Pro Ile Ser
1               5                   10                  15

Lys Asp Arg Lys Glu Arg Val His Gln Gly Met Val Arg Ala Ala Thr
            20                  25                  30

Val Gly Tyr Gly Ile Leu Arg Glu Gly Gly Ser Ala Val Asp Ala Val
        35                  40                  45

Glu Gly Ala Val Val Ala Leu Glu Asp Asp Pro Glu Phe Asn Ala Gly
    50                  55                  60

Cys Gly Ser Val Leu Asn Thr Asn Gly Glu Val Glu Met Asp Ala Ser
65                  70                  75                  80

Ile Met Asp Gly Lys Asp Leu Ser Ala Gly Ala Val Ser Ala Val Gln
                85                  90                  95

Cys Ile Ala Asn Pro Ile Lys Leu Ala Arg Leu Val Met Glu Lys Thr
            100                 105                 110
```

Pro His Cys Phe Leu Thr Asp Gln Gly Ala Ala Gln Phe Ala Ala Ala
            115                 120                 125

Met Gly Val Pro Glu Ile Pro Gly Glu Lys Leu Val Thr Glu Arg Asn
130                 135                 140

Lys Lys Arg Leu Glu Lys Glu Lys His Glu Lys Gly Ala Gln Lys Thr
145                 150                 155                 160

Asp Cys Gln Lys Asn Leu Gly Thr Val Gly Ala Val Ala Leu Asp Cys
                165                 170                 175

Lys Gly Asn Val Ala Tyr Ala Thr Ser Thr Gly Gly Ile Val Asn Lys
            180                 185                 190

Met Val Gly Arg Val Gly Asp Ser Pro Cys Leu Gly Ala Gly Gly Tyr
            195                 200                 205

Ala Asp Asn Asp Ile Gly Ala Val Ser Thr Thr Gly His Gly Glu Ser
210                 215                 220

Ile Leu Lys Val Asn Leu Ala Arg Leu Thr Leu Phe His Ile Glu Gln
225                 230                 235                 240

Gly Lys Thr Val Glu Glu Ala Ala Asp Leu Ser Leu Gly Tyr Met Lys
                245                 250                 255

Ser Arg Val Lys Gly Leu Gly Gly Leu Ile Val Val Ser Lys Thr Gly
                260                 265                 270

Asp Trp Val Ala Lys Trp Thr Ser Thr Ser Met Pro Trp Ala Ala Ala
            275                 280                 285

Lys Asp Gly Lys Leu His Phe Gly Ile Asp Pro Asp Asp Thr Thr Ile
290                 295                 300

Thr Asp Leu Pro
305

<210> SEQ ID NO 6
<211> LENGTH: 927
<212> TYPE: DNA
<213> ORGANISM: Homo sapiens

<400> SEQUENCE: 6
atgaatccca tcgtagtggt ccacggcggc ggagccggtc ccatctccaa ggatcggaag     60
gagcgagtgc accagggcat ggtcagagcc gccaccgtgg gctacggcat cctccgggag    120
ggcgggagcg ccgtggatgc cgtagaggga gctgtcgtcg ccctggaaga cgatcccgag    180
ttcaacgcag gttgtgggtc tgtcttgaac acaaatggtg aggttgaaat ggatgctagt    240
atcatggatg gaaaagacct gtctgcagga gcagtgtccg cagtccagtg tatagcaaat    300
cccattaaac ttgctcggct tgtcatggaa aagacacctc attgctttct gactgaccaa    360
ggcgcagcgc agtttgcagc agctatgggg gttccagaga ttcctggaga aaaactggtg    420
acagagagaa acaaaaagcg cctggaaaaa gagaagcatg aaaaaggtgc tcagaaaaca    480
gattgtcaaa aaaacttggg aaccgtgggt gctgttgcct ggactgcaa agggaatgta    540 gcctacgcaa cctccacagg cggtatcgtt aataaaatgg tcggccgcgt tggggactca    600
ccgtgtctag gagctggagg ttatgccgac aatgacatcg gagccgtctc aaccacaggg    660
catggggaaa gcatcctgaa ggtgaacctg ctagactca ccctgttcca catagaacaa    720
ggaaagacgg tagaagaggc tgcggaccta tcgttgggtt atatgaagtc aagggttaaa    780
ggtttaggtg gcctcatcgt ggttagcaaa acaggagact gggtggcaaa gtggacctcc    840
acctccatgc cctgggcagc cgccaaggac ggcaagctgc acttcggaat tgatcctgac    900
gatactacta tcaccgacct tccctaa                                       927

<210> SEQ ID NO 7
<211> LENGTH: 378
<212> TYPE: PRT
<213> ORGANISM: Artificial Sequence
<220> FEATURE:
<223> OTHER INFORMATION: consensus sequence

<400> SEQUENCE: 7

Gly Thr Leu Leu Ile Ala Ile His Gly Leu Glu Ala Gly Asp Ile
 1               5                  10                  15

Asp Ser Ser Glu Pro Lys Thr Thr Asn Leu Pro Leu Val Leu Thr Thr
                20                  25                  30

Trp Arg Ser Glu Ala Leu Lys His Ala Val Glu Ala Ala Trp Lys Ala
                35                  40                  45

Leu Lys Ala Gly Gly Ser Ala Leu Asp Ala Val Glu Lys Gly Val Arg
50                  55                  60

Leu Leu Glu Asn Glu Pro Cys Asp Phe Asn Ala Gly Tyr Gly Gly Val
65                  70                  75                  80

Leu Asp Glu Asp Gly Thr Val Glu Leu Asp Ala Ser Ile Met Asp Gly
                85                  90                  95

Asn Thr Ser Ser Ser Met Val Val Ile Glu Asn Ile Phe Cys Arg Asp
                100                 105                 110

Gly Met Lys Val Gly Ala Val Ala Gly Leu Ser Arg Ile Lys Asn Pro
                115                 120                 125

Ile Ser Val Ala Arg Leu Val Met Glu Lys Thr Pro His Ile Leu Leu
                130                 135                 140

Val Gly Glu Gly Ala Glu Glu Phe Ala Lys Ser Gln Gly Phe Glu Thr
145                 150                 155                 160

Glu Asp Leu Ser Thr Phe Glu Thr Gln Glu Trp Ile Glu Glu Trp Leu
                165                 170                 175

Ala Ala Lys Glu Gln Lys Asn Tyr Trp Lys Arg Val Ile Leu Asp Pro
                180                 185                 190

Ser Val Tyr Cys Gly Pro Tyr Lys Thr Pro Gly Leu Leu Lys Ser Glu
                195                 200                 205

Arg Asp Ile Pro Leu Asp Asn Glu Asp Ser Glu Ala Gly Tyr Leu Val
                210                 215                 220

Asp Asp Arg Gln His Gly Thr Ile Gly Met Val Ala Leu Asp Ala Glu
225                 230                 235                 240

Gly Asn Leu Ala Ala Ala Thr Ser Thr Gly Gly Met Val Asn Lys Met
                245                 250                 255

His Gly Arg Val Gly Asp Ser Pro Ile Ile Gly Ala Gly Ala Tyr Ala
                260                 265                 270

Asn Asn Phe Ala Gly Ala Val Ser Ala Thr Gly Lys Gly Glu Val Ile
                275                 280                 285

Ile Arg Ala Leu Pro Ala Tyr Asp Val Val Ala Leu Met Glu Tyr Gly
                290                 295                 300

Gly Lys Pro Leu Ser Leu Ala Glu Ala Ala Lys Arg Ile Thr Lys
305                 310                 315                 320

Ala Leu Pro Lys Arg Gly Lys Asn Leu Lys Asp Gly Ser Gly Gly Leu
                325                 330                 335

Ile Ala Leu Asn His Lys Gly Glu Ile Ala Ala Pro Cys Asn Thr Thr
                340                 345                 350

Gly Met Phe Arg Ala Ala His Thr Ala Thr Glu Asp Gly Thr Thr Leu
                355                 360                 365

```
Glu Tyr Ser Glu Ile Gly Ile Trp Glu Lys
    370                 375

<210> SEQ ID NO 8
<211> LENGTH: 9
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 1
<223> OTHER INFORMATION: Xaa = Leu, Ile, Val, or Met
<220> FEATURE:
<221> NAME/KEY: VARIANT
<222> LOCATION: 2, 3
<223> OTHER INFORMATION: Xaa = Any Amino Acid
<220> FEATURE:
<221> NAME/KEY: VARIANT
<222> LOCATION: 8
<223> OTHER INFORMATION: Xaa = Ile or Val
<220> FEATURE:
<221> NAME/KEY: VARIANT
<222> LOCATION: 9
<223> OTHER INFORMATION: Xaa = Ala, Gly, or Ser

<400> SEQUENCE: 8

Xaa Xaa Xaa Thr Gly Gly Thr Xaa Xaa
  1               5

<210> SEQ ID NO 9
<211> LENGTH: 11
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 2, 4-5
<223> OTHER INFORMATION: Xaa = Any Amino Acid
<220> FEATURE:
<221> NAME/KEY: VARIANT
<222> LOCATION: 3, 11
<223> OTHER INFORMATION: Xaa = Leu, Ile, Val, or Met

<400> SEQUENCE: 9

Gly Xaa Xaa Xaa Xaa His Gly Thr Asp Thr Xaa
  1               5                  10
```

HUMAN HYDROLASE FAMILY MEMBERS AND USES THEREOF

RELATED APPLICATIONS

This application is divisional of U.S. application Ser. No. 10/193,452, filed Jul. 11, 2002, now abandoned which is a continuation-in-part and claims priority to U.S. application Ser. No. 09/816,664, filed Mar. 23, 2001 (abandoned), which claims the benefit of U.S. Provisional Application Ser. No. 60/191,973, filed Mar. 24, 2000 (abandoned); and U.S. Application Ser. No. 09/841,880, filed Apr. 24, 2001 (abandoned), which claims the benefit of U.S. Provisional Application Ser. No. 60/1 99,559, filed Apr. 25, 2000 (abandoned); and U.S. application Ser. No. 09/862,556, filed May 22, 2001 (abandoned), which claims the benefit of U.S. Provisional Application Ser. No. 60/206,036, filed May 22, 2000 (abandoned); and U.S. application Ser. No. 09/861,165, filed May 18, 2001 (abandoned), which claims the benefit of U.S. Provisional Application Ser. No. 60/205,442, filed May 19, 2000 (abandoned); and U.S. application Ser. No. 09/875,353, filed Jun. 6, 2001 (abandoned), which claims the benefit of U.S. Provisional Application Ser. No. 60/209,949, filed Jun. 6, 2000 (abandoned); and U.S. Application Ser. No. 09/896,578, filed Jun. 29, 2001 (abandoned), which claims the benefit of U.S. Provisional Application Ser. No. 60/214,948, filed Jun. 29, 2000 (abandoned); and U.S. application Ser. No. 09/911,150, filed Jul. 23, 2001 (abandoned), which claims the benefit of U.S. Provisional Application Ser. No. 60/220,008, filed Jul. 21, 2000 (abandoned); and U.S. application Ser. No. 09/911,317, filed Jul. 23, 2001 (abandoned), which claims the benefit of U.S. Provisional Application Ser. No. 60/220,040, filed Jul. 21, 2000 (abandoned); and U.S. application Ser. No. 09/934,323, filed Aug. 21, 2001 (abandoned), which claims the benefit of U.S. Provisional Application Ser. No. 60/226,774, filed Aug. 21, 2000 (abandoned); and U.S. Application Ser. No. 09/963,959, filed Sep. 25, 2001 (abandoned), which claims the benefit of U.S. Provisional Application Ser. No. 60/235,033, filed Sep. 25, 2000 (abandoned); and U.S. application Ser. No. 09/971,490, filed Oct. 5, 2001 (abandoned), and which claims the benefit of U.S. Provisional Application Ser. No. 60/238,170, filed Oct. 5, 2000 (abandoned); and U.S. application Ser. No. 10/071,275, filed Feb. 7, 2002 (abandoned), which claims the benefit of U.S. Provisional Application Ser. No. 60/267,054, filed Feb. 7, 2001 (abandoned); and U.S. application Ser. No. 09/888,911, filed Jun. 25, 2001 (abandoned), which claims the benefit of U.S. Provisional Application Ser. No. 60/213,688, filed Jun. 23, 2000 (abandoned). The entire contents of each of these applications are incorporated herein by reference.

BACKGROUND OF THE 26443 AND 46873 INVENTION

Asparaginase is an enzyme that catalyzes the hydrolysis of asparagine to aspartic acid and ammonia. *Saccharomyces cerevisiae* expresses two forms of asparaginase: L-asparaginase I, a cytoplasmic enzyme that is synthesized constitutively, and asparaginase II, a cell wall mannan protein localized external to the cell membrane which plays a role in hydrolysis of exogenous asparagines and uptake of aspartic acid. The two enzymes are biochemically and genetically distinct.

Because some lymphoid tumor cells are deficient in L-asparagine synthetase and cannot synthesize sufficient L-asparagine, asparagine is, for these cells, an essential amino acid. Therefore, asparagine depletion by administration of asparaginase rapidly results in decreased protein synthesis, followed by a decrease in DNA and RNA synthesis, and ultimately cell death.

SUMMARY OF THE 26443 AND 46873 INVENTION

The present invention is based, in part, on the discovery of novel asparaginases, referred to herein as "26443" and "46873" nucleic acid and protein molecules. The nucleotide sequence of a cDNA encoding 26443 and 46873 is shown in SEQ ID NO: 1 and SEQ ID NO:4, respectively, and the amino acid sequence of a 26443 and 46873 polypeptide is shown in SEQ ID NO:2 and SEQ ID NO:5, respectively. In addition, the nucleotide sequence of the coding regions of 26443 and 46873 are depicted in SEQ ID NO:3 and SEQ ID NO:6, respectively.

Accordingly, in one aspect, the invention features a nucleic acid molecule that encodes a 26443 or 46873 protein or polypeptide, e.g., a biologically active portion of the 26443 or 46873 protein. In a preferred embodiment the isolated nucleic acid molecule encodes a polypeptide having the amino acid sequence of SEQ ID NO:2 or SEQ ID NO:5. In other embodiments, the invention provides isolated 26443 or 46873 nucleic acid molecules having the nucleotide sequence shown in SEQ ID NO:1, SEQ ID NO:3, SEQ ID NO:4 or SEQ ID NO:6. In still other embodiments, the invention provides nucleic acid molecules that are substantially identical (e.g., naturally occurring allelic variants) to the nucleotide sequence shown in SEQ ID NO:1, SEQ ID NO:3, SEQ ID NO:4 or SEQ ID NO:6. In other embodiments, the invention provides a nucleic acid molecule which hybridizes under stringent hybridization conditions to a nucleic acid molecule comprising the nucleotide sequence of SEQ ID NO:1, SEQ ID NO:3, SEQ ID NO:4 or SEQ ID NO:6, wherein the nucleic acid encodes a full length 26443 or 46873 protein or a biologically active fragment thereof.

In a related aspect, the invention further provides nucleic acid constructs, which include a 26443 or 46873 nucleic acid molecule described herein. In certain embodiments, the nucleic acid molecules of the invention are operatively linked to native or heterologous regulatory sequences. Also included, are vectors and host cells containing the 26443 or 46873 nucleic acid molecules of the invention e.g., vectors and host cells suitable for producing 26443 or 46873 nucleic acid molecules and polypeptides.

In another related aspect, the invention provides nucleic acid fragments suitable as primers or hybridization probes for the detection of 26443 or 46873-encoding nucleic acids.

In still another related aspect, isolated nucleic acid molecules that are antisense to a 26443 or 46873 encoding nucleic acid molecule are provided.

In another aspect, the invention features, 26443 or 46873 polypeptides, and biologically active or antigenic fragments thereof that are useful, e.g., as reagents or targets in assays applicable to treatment and diagnosis of 26443- or 46873-mediated or related disorders. In another embodiment, the invention provides 26443 or 46873 polypeptides having a 26443 or 46873 activity. Preferred polypeptides are 26443 or 46873 proteins including at least one asparaginase domain, and, preferably, having a 26443 or 46873 activity, e.g., a 26443 or 46873 activity as described herein.

In other embodiments, the invention provides 26443 or 46873 polypeptides, e.g., a 26443 or 46873 polypeptide having the amino acid sequence shown in SEQ ID NO:2 or SEQ ID NO:5, respectively; an amino acid sequence that is substantially identical to the amino acid sequence shown in SEQ ID NO:2 or SEQ ID NO:5; or an amino acid sequence encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:4 or SEQ ID NO:6, wherein the nucleic acid encodes a full length 26443 or 46873 protein or an active fragment thereof.

In a related aspect, the invention further provides nucleic acid constructs that include a 26443 or 46873 nucleic acid molecule described herein.

In a related aspect, the invention provides 26443 or 46873 polypeptides or fragments operatively linked to non-26443 or -46873 polypeptides to form fusion proteins.

In another aspect, the invention features antibodies and antigen-binding fragments thereof, that react with, or more preferably, specifically bind 26443 or 46873 polypeptides.

In another aspect, the invention provides methods of screening for compounds that modulate the expression or activity of the 26443 or 46873 polypeptides or nucleic acids.

In still another aspect, the invention provides a process for modulating 26443 or 46873 polypeptide or nucleic acid expression or activity, e.g., using the screened compounds. In certain embodiments, the methods involve treatment of conditions related to aberrant activity or expression of the 26443 or 46873 polypeptides or nucleic acids, such as metabolic diseases and conditions involving aberrant or deficient oxidation of long- and medium-chain fatty acids.

The invention also provides assays for determining the activity of, or the presence or absence of, 26443 or 46873 polypeptides or nucleic acid molecules in a biological sample, including for the purpose of disease diagnosis.

In a further aspect, the invention provides assays for determining the presence or absence of a genetic alteration in a 26443 or 46873 polypeptide or nucleic acid molecule, including for the purpose of disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 26443 or 46873 molecule. In one embodiment, the capture probe is a nucleic acid, e.g., a probe complementary to a 26443 or 46873 nucleic acid sequence. In another embodiment, the capture probe is a polypeptide, e.g., an antibody specific for 26443 or 46873 polypeptides. Also featured is a method of analyzing a sample by contacting the sample to the aforementioned array and detecting binding of the sample to the array.

Other features and advantages of the invention will be apparent from the following detailed description, and from the claims.

BRIEF DESCRIPTION OF THE DRAWINGS

FIGS. 1A–1B depicts a cDNA sequence (SEQ ID NO: 1) and predicted amino acid sequence (SEQ ID NO:2) of human 26443. The methionine-initiated open reading frame of human 26443 (without the 5' and 3' untranslated regions) starts at nucleotide 91 and continues through to nucleotide 1344 of SEQ ID NO: 1 (coding sequence also shown in SEQ ID NO:3).

FIG. 4 depicts an alignment of the asparaginase domain of human 26443 with a consensus amino acid sequence derived from a hidden Markov model. The upper sequence is the consensus amino acid sequence (SEQ ID NO:7), while the lower amino acid sequence corresponds to amino acids 38 to 345 of SEQ ID NO:2.

FIG. 5 depicts a cDNA sequence (SEQ ID NO:4) and predicted amino acid sequence (SEQ ID NO:5) of human 46873. The methionine-initiated open reading frame of human 46873 (without the 5' and 3' untranslated regions) starts at nucleotide 134 and continues through to nucleotide 1057 of SEQ ID NO:4 (coding sequence also shown in SEQ ID NO:6).

Figure 2:
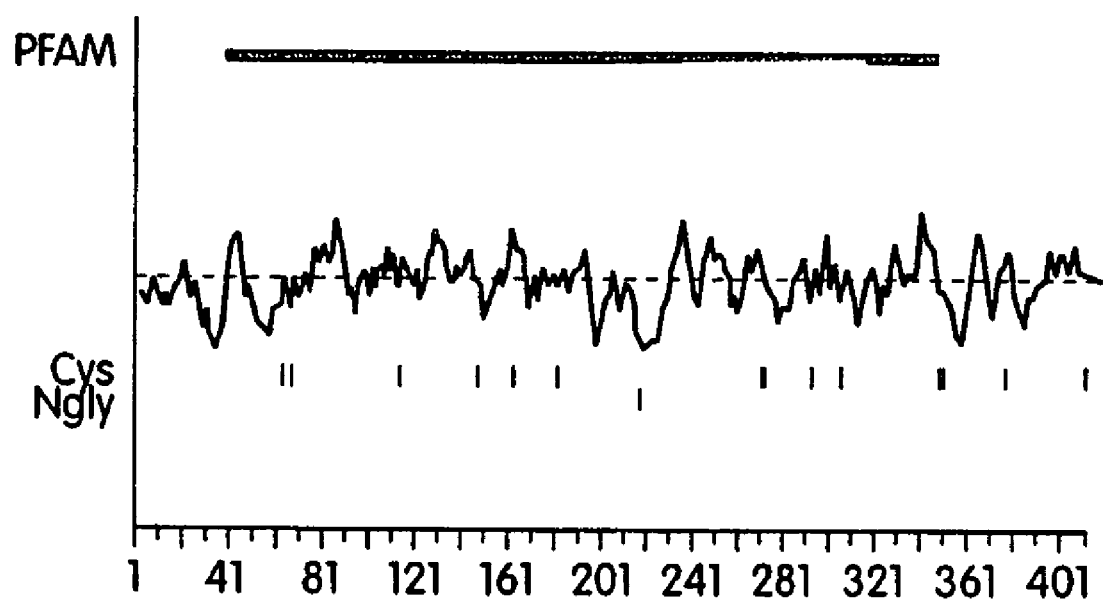
FIG. 2 depicts a hydropathy plot of human 26443. Relative hydrophobic residues are shown above the dashed horizontal line, and relative hydrophilic residues are below the dashed horizontal line. The cysteine residues (Cys) are indicated by short vertical lines just below the hydropathy trace. The numbers corresponding to the amino acid sequence of human 26443 are indicated. Polypeptides of the invention include 26443 fragments that include: all or part of a hydrophobic sequence (a sequence above the dashed line; all or part of a hydrophilic fragment (e.g., a fragment below the dashed line). Other fragments include a cysteine or a glycosylation site.
Figure 3:
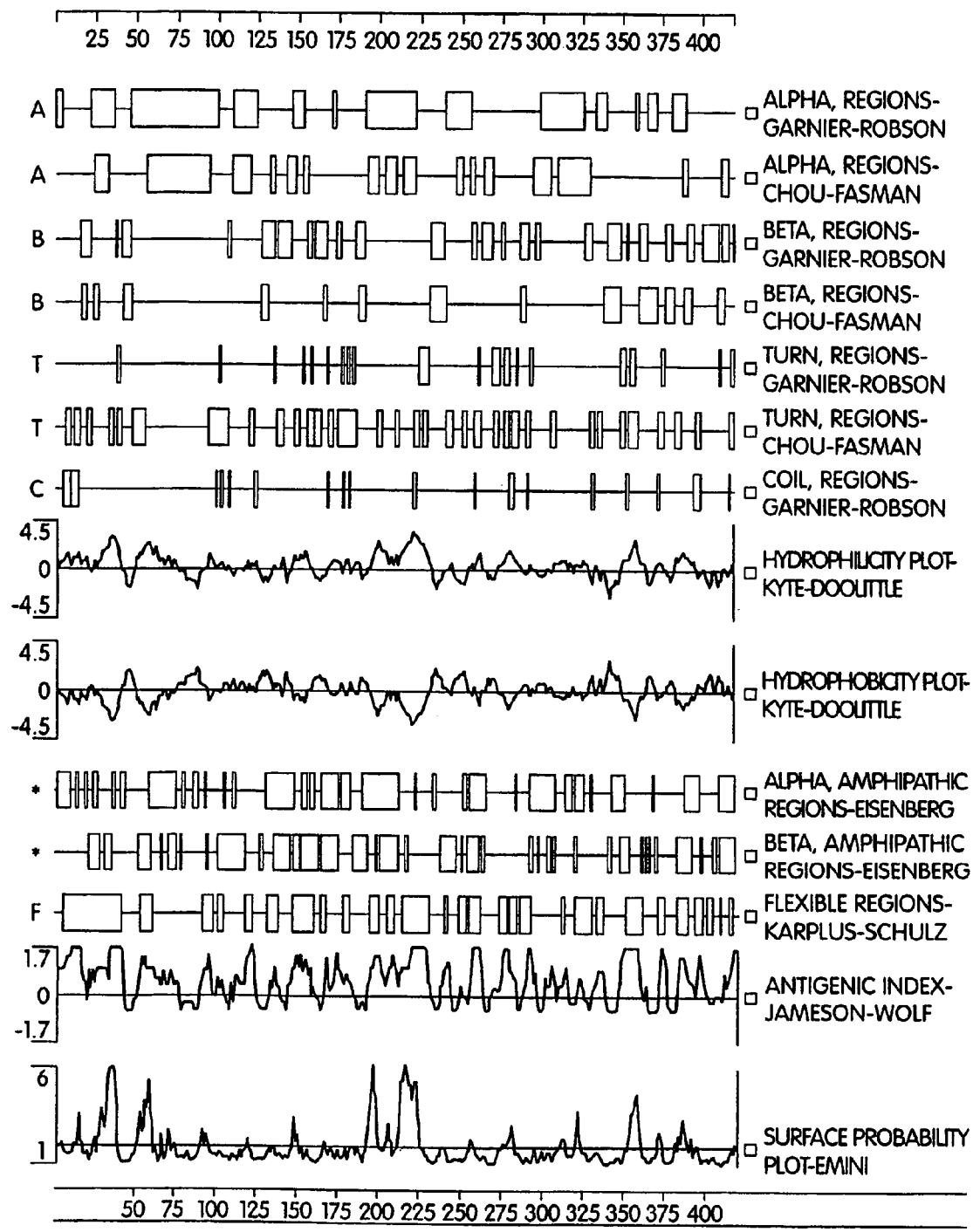
FIG. 3 depicts a series of plots summarizing an analysis of the primary and secondary protein structure of a human asparaginase. The particular algorithm used for each plot is indicated at the right hand side of each plot. The following plots are depicted: Garnier-Robson plots providing the predicted location of alpha-, beta-, turn and coil regions (Garnier et al. (1978) J. Mol. Biol. 120:97); Chou-Fasman plots providing the predicted location of alpha-, beta-, turn and coil regions (Chou and Fasman (1978) Adv. In Enzymol. Mol. 47:45–148); Kyte-Doolittle hydrophilicity/hydrophobicity plots (Kyte and Doolittle (1982) J. Mol. Biol. 157: 105–132); Eisenberg plots providing the predicted location of alpha- and beta-amphipathic regions (Eisenberg et al. (1982) Nature 299:371–374); a Karplus-Schultz plot providing the predicted location of flexible regions (Karplus and Schulz (1985) Naturwissens-Chafen 72:212–213); a plot of the antigenic index (Jameson-Wolf) (Jameson and Wolf (1988) CABIOS 4:121–136); and a surface probability plot (Emini algorithm) (Emini et al. (1985) J. Virol. 55:836–839). The numbers corresponding to the amino acid sequence of human 26443 are indicated.
Figure 6:
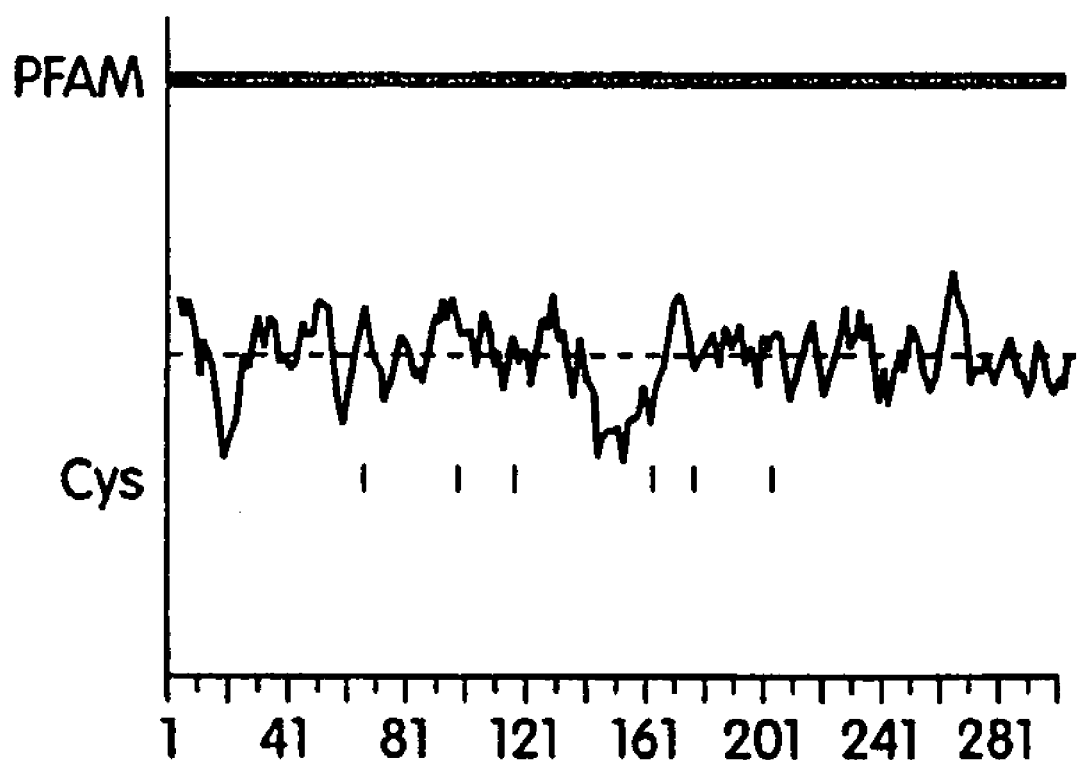
FIG. 6 depicts a hydropathy plot of human 46873. Relative hydrophobic residues are shown above the dashed horizontal line, and relative hydrophilic residues are below the dashed horizontal line. The cysteine residues (Cys) are indicated by short vertical lines just below the hydropathy trace. The numbers corresponding to the amino acid sequence of human 46873 are indicated. Polypeptides of the invention include 46873 fragments that include: all or part of a hydrophobic sequence (a sequence above the dashed line; all or part of a hydrophilic fragment (e.g., a fragment below the dashed line).
Figure 7:
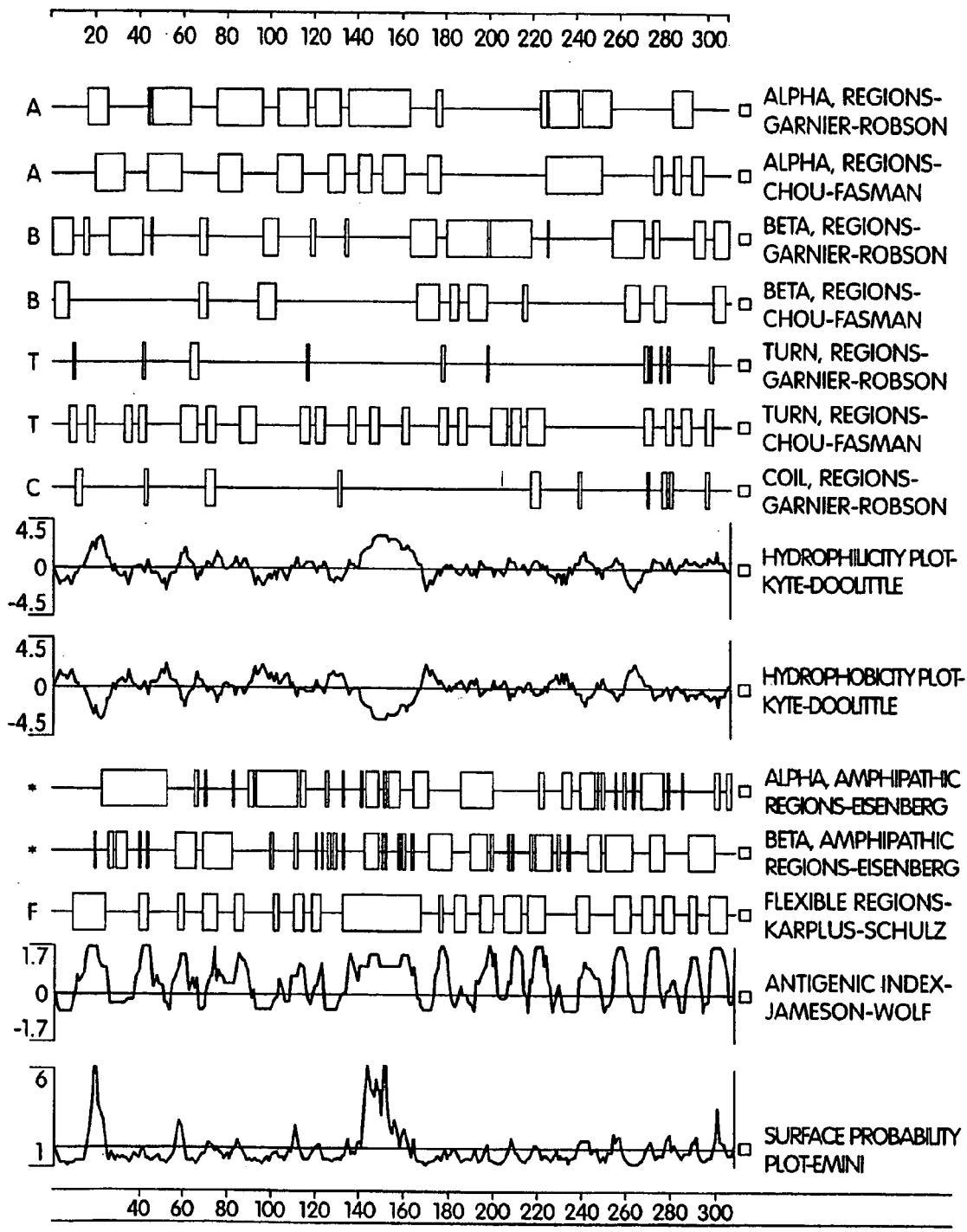
FIG. 7 depicts a series of plots summarizing an analysis of the primary and secondary protein structure of a human asparaginase. The particular algorithm used for each plot is indicated at the right hand side of each plot. The following plots are depicted: Garnier-Robson plots providing the predicted location of alpha-, beta-, turn and coil regions (Garnier et al. (1978) J. Mol. Biol. 120:97); Chou-Fasman plots providing the predicted location of alpha-, beta-, turn and coil regions (Chou and Fasman (1978) Adv. In Enzymol. Mol. 47:45–148); Kyte-Doolittle hydrophilicity/hydrophobicity plots (Kyte and Doolittle (1982) J. Mol. Biol. 157: 105–132); Eisenberg plots providing the predicted location of alpha- and beta-amphipathic regions (Eisenberg et al.

(1982) Nature 299:371–374); a Karplus-Schultz plot providing the predicted location of flexible regions (Karplus and Schulz (1985) Naturwissens-Chafen 72:212–213); a plot of the antigenic index (Jameson-Wolf) (Jameson and Wolf (1988) CABIOS 4:121–136); and a surface probability plot (Emini algorithm) (Emini et al. (1985) J. Virol. 55:836–839). The numbers corresponding to the amino acid sequence of human 46873 are indicated.

FIG. 8 depicts an alignment of the asparaginase domain of human 46873 with a consensus amino acid sequence derived from a hidden Markov model. The upper sequence is the consensus amino acid sequence (SEQ ID NO:7), while the lower amino acid sequence corresponds to amino acids 1 to 302 of SEQ ID NO:5.

DETAILED DESCRIPTION OF 26443 AND 46873

The human 26443 sequence (FIG. 1; SEQ ID NO: 1), which is approximately 1888 nucleotides long, including untranslated regions, contains a predicted methionine-initiated coding sequence of about 1254 nucleotides (SEQ ID NO:3, and nucleotides 91–1344 of SEQ ID NO: 1). The coding sequence encodes an 418 amino acid protein (SEQ ID NO:2).

Human 26443 contains a predicted asparaginase domain from about amino acids 38 to 345 of SEQ ID NO:2.

The 26443 protein also includes the following domains: a predicted N-glycosylation site (PFAM Accession PS0001) located at about amino acid residues 225–228 of SEQ ID NO:2; two predicted glycosaminoglycan attachment sites (PFAM Accession PS0002) located at about amino acid residues 7–10 and 289–292 of SEQ ID NO:2; a predicted cAMP- and cGMP-dependent protein kinase phosphorylation site (PFAM Accession PS0004) located at about amino acid residues 217–220 of SEQ ID NO:2; five predicted Protein Kinase C phosphorylation sites (PS00005) at about amino acids 24–26, 33–35, 186–188, 221–223 and 346–348 of SEQ ID NO:2; six predicted Casein Kinase II phosphorylation sites (PS00006) located at about amino acids 6–9, 24–27, 33–36, 116–119, 221–224 and 381–384 of SEQ ID NO:2; and eight predicted N-myristoylation sites (PS00008) from about amino acids 4–9, 77–82, 100–105, 126–131, 228–233, 242–247, 336–341 and 397–402 of SEQ ID NO:2.

The human 46873 sequence (FIG. 4; SEQ ID NO:4), which is approximately 1358 nucleotides long, including untranslated regions, contains a predicted methionine-initiated coding sequence of about 924 nucleotides (SEQ ID NO:6, and nucleotides 134–1057 of SEQ ID NO:4). The coding sequence encodes a 308 amino acid protein (SEQ ID NO:5).

Human 46873 contains a predicted asparaginase domain from about amino acids 1 to 302 of SEQ ID NO:5.

The 46873 protein also includes the following domains: one predicted Protein Kinase C phosphorylation site (PS00005) at about amino acids 141–143 of SEQ ID NO:5; five predicted Casein Kinase II phosphorylation sites (PS00006) located at about amino acids 43–46, 71–74, 80–83, 243–246 and 303–306 of SEQ ID NO:5; and eight predicted N-myristoylation sites (PS00008) from amino acids 26–31, 50–55, 66–71, 90–05, 156–161, 167–172, 187–192 and 214–219 of SEQ ID NO:5.

For general information regarding PFAM identifiers, PS prefix and PF prefix domain identification numbers, refer to Sonnhammer et al. (1997) *Protein* 28:405–420.

TABLE 1

Summary of Sequence Information for Asparaginase Polypeptides

| GENE | cDNA | ORF | Polypeptide | FI |
|---|---|---|---|---|
| 26443 | SEQ ID NO:1 | SEQ ID NO:3 | SEQ ID NO:2 | 1 |
| 46873 | SEQ ID NO:4 | SEQ ID NO:6 | SEQ ID NO:5 | 5 |

The 26443 and 46873 proteins contain a significant number of structural characteristics in common with members of the asparaginase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

26443 and 46873 polypeptides or 26443 and 46873 family members can include an "asparaginase domain" or regions homologous with an "asparaginase domain".

As used herein, the term "asparaginase domain" refers to a protein domain having an amino acid sequence of about 50 to 600 amino acids, preferably about 150 to 450 amino acid residues, more preferably about 300 to 310 amino acids. An asparaginase domain typically includes two conserved threonine residues that play a role in the catalytic properties of asparaginases. The first is typically located in the N-terminal extremity of the protein, while the second is located at the end of the first third of the amino acid sequence. Consensus patterns for asparaginases are as follows: [LIVM]-x(2)-T-G-G-T-[IV]-[AGS], SEQ ID NO:8, the second T is an active site residue, and G-x-[LIVM]-x(2)-H-G-T-D-T-[LIVM], SEQ ID NO:9, wherein the first T is an active site residue. Preferably, an "asparaginase domain" includes an amino acid sequence of about 250 to 400 amino acid residues in length and having a bit score for the alignment of the sequence to the asparaginase domain (HMM) of at least 75. More preferably, an asparaginase domain includes at least about 50 to 600 amino acids, even more preferably about 150 to 400 amino acids, or even most preferably, 300–310 amino acids, and has a bit score for the alignment of the sequence to the asparaginase domain (HMM) of at least 75, 100, 200, 300, 400 or greater. Asparaginase domains (HMM) have been assigned PFAM Accession PF00710 and PFAM Accession PF01112. An alignment of the asparaginase domain (SEQ ID NO:7, corresponding to amino acids 38 to 345 of SEQ ID NO:2) of human 26443 with a consensus amino acid sequence derived from a hidden Markov model is depicted in FIG. 4. An alignment of the asparaginase domain (SEQ ID NO:7, corresponding to amino acids 1 to 302 of SEQ ID NO:5) of human 46873 with a consensus amino acid sequence derived from a hidden Markov model is depicted in FIG. 8.

In a preferred embodiment, A 26443 or 46873 polypeptide or protein has an "asparaginase domain" or a region which includes at least about 50–600, more preferably about 150–450 or 300–310 amino acid residues, and having at least about 60%, 70% 80% 90% 95%, 99%, or 100% homology with an "asparaginase domain," e.g., the asparaginase domain of human 26443 or 46873 (e.g., residues 38–345 of SEQ ID NO:2 or residues 1–302 of SEQ ID NO:5, respectively).

To identify the presence of a "asparaginase domain" in a 26443 or 46873 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28(3): 405–420 and a detailed description of HMMs can be found, for example, in Gribskov et al.(1990) Meth. Enzymol. 183: 146–159; Gribskov et al.(1987) Proc. Natl. Acad. Sci. USA 84:4355–4358; Krogh et al.(1994) J. Mol. Biol. 235:1501–1531; and Stultz et al.(1993) Protein Sci. 2:305–314, the contents of which are incorporated herein by reference. A search was performed against the HMM database resulting in the identification of an "asparaginase domain" in the amino acid sequence of human 26443 and 46873 at about residues 38–345 of SEQ ID NO:2 (see FIG. 4) and 1–302 of SEQ ID NO:5 (see FIG. 8), respectively.

As the 26443 or 46873 polypeptides of the invention may modulate 26443- or 46873-mediated activities, they may be useful as, or for, developing novel diagnostic and therapeutic agents for 26443- or 46873-mediated or related disorders, as described below.

As used herein, a "26443 or 46873 activity", "biological activity of 26443 or 46873" or "functional activity of 26443 or 46873", refers to an activity exerted by a 26443 or 46873 protein, polypeptide or nucleic acid molecule on, e.g., a 26443- or 46873-responsive cell or on a 26443 or 46873 substrate, e.g., a protein substrate, as determined in vivo or in vitro. In one embodiment, a 26443 or 46873 activity is a direct activity, such as an association with a 26443 or 46873 target molecule. A "target molecule" or "binding partner" is a molecule with which a 26443 or 46873 protein binds or interacts in nature. In an exemplary embodiment, a "target molecule" is, e.g., an asparagine. A 26443 or 46873 activity can also be an indirect activity, e.g., a cellular signaling activity mediated by interaction of the 26443 or 46873 protein with a 26443 or 46873 ligand. For example, the 26443 or 46873 proteins of the present invention can have one or more of the following activities: (1) catalyzes the hydrolysis of asparagine to aspartic acid and ammonia; (2) regulates cellular amounts of asparagine; (3) regulates the cellular amounts of aspartic acid; (4) regulates cellular amounts of ammonia; and (5) antagonizes or inhibits, e.g., competitively or noncompetitively, any of activities 1–4.

Based on the above-described sequence similarities, the 26443 or 46873 molecules of the present invention are predicted to have similar biological activities as asparaginase family members. Asparaginase enzymes assist in the hydrolysis of asparagine to aspartic acid and ammonia. Thus, the 26443 or 46873 molecules can act as novel diagnostic targets and therapeutic agents for controlling, e.g., the amount of asparagine (and likewise, aspartic acid) in a cell.

The 26443 or 46873 protein may be involved in disorders characterized by aberrant activity of the cells in which it is expressed. Since asparaginase enzymes are typically found in most cells in bacterial fungi, plants and mammals, e.g., cells that contain or metabolize asparagine, it is likely that 26443 or 46873 proteins may also be expressed in such cells. Therefore, altered expression and/or activity of a 26443 or 46873 molecule can lead to defects in the metabolism of asparagine and/or aspartic acid.

The 26443 or 46873 molecules can also act as novel diagnostic targets and therapeutic agents for controlling one or more of cellular proliferative and/or differentiative disorders, disorders associated with bone metabolism, immune disorders, hematopoietic disorders, cardiovascular disorders, liver disorders, viral diseases, pain or metabolic disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The 26443 or 46873 nucleic acid and protein of the invention can be used to treat and/or diagnose a variety of hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Asparaginases are generally more effective in treating acute lymphoblastic leukemia and lymphosarcomas, than other forms of leukemia or solid tumors, since remissions of these types of cancers are invariably of short duration. Whereas most normal tissues synthesize L-asparagine in amounts sufficient for their metabolic needs, certain neoplastic tissues, primarily acute lymphoblastic leukemia (ALL) and lymphosarcoma cells, require an exogenous source of asparagines (i.e., from nearby host tissues). Administration of L-asparaginase enzymatically catalyzes the hydrolysis of asparagine to aspartic acid and ammonia, which deprives the malignant cells of the asparagine from extracellular fluid and eventually results in cell death. Clinical use of asparaginase from, e.g., *Escherichia coli* or *Erwinia chrysanthemi,* often times results in hypersensitive immune responses after multiple administrations. Since the two asparaginase enzymes from *E. coli* and *E. chrysanthemi* do not exhibit any cross-reactivity, the two enzymes can be used in a treatment regimen to reduce or avoid the hypersensitivity response.

Additionally, asparaginases can be administered in combination with other traditional or experimental cancer treatments. Asparaginases can be combined with a treatment modality which inhibits cell proliferation, e.g., cytotoxic agents, e.g., agents with diverse structures and mechanisms of action, including but not limited to, antimicrotubule agents, topoisomerase I inhibitors, topoisomerase II inhibitors, antimetabolites, mitotic inhibitors, alkylating agents, intercalating agents, agents capable of interfering with a signal transduction pathway (e.g., protein kinase C inhibitors, e.g., anti-hormones, e.g., antibodies against growth factor receptors), agents that promote apoptosis and/or necrosis, biological response modifiers (e.g., interferons, interleukins, tumor necrosis factors), and radiation.

The 26443 or 46873 protein, fragments thereof, and derivatives and other variants of the sequence in SEQ ID NO:2 or SEQ ID NO:5, respectively, are collectively referred to as "polypeptides or proteins of the invention" or "26443 or 46873 polypeptides or proteins". Nucleic acid molecules encoding such polypeptides or proteins are collectively referred to as "nucleic acids of the invention" or "26443 or 46873 nucleic acids". 26443 or 46873 molecules refer to 26443 or 46873 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules that are separated from other nucleic acid molecules that are present in the natural source of the nucleic acid. For example, with regards to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology,* John Wiley & Sons, N.Y. (1989), 6.3.1-6.3.6, which is incorporated by reference. Aqueous and non-aqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. Preferably, an isolated nucleic acid molecule of the invention that hybridizes under stringent conditions to the sequence of SEQ ID NO: 1 or 3, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 26443 or 46873 protein, preferably a mammalian 26443 or 46873 protein, and can further include non-coding regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 26443 or 46873 protein having less than about 30%, 20%, 10% and more preferably 5% (by dry weight), of non-26443 or -46873 protein (also referred to herein as a "contaminating protein"), or of chemical precursors or non- 26443 or -46873 chemicals. When the 26443 or 46873 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 26443 or 46873 (e.g., the nucleotide sequence of SEQ ID NO:1, SEQ ID NO:3, SEQ ID NO:4 or SEQ ID NO:6, without abolishing or more preferably, without substantially altering a biological activity, whereas an "essential" amino acid residue results in such a change. For example, amino acid residues that are conserved among the polypeptides of the present invention, e.g., those present in the asparaginase domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 26443 or 46873 protein is preferably replaced with another amino acid residue from the same side chain family. Alternatively, in another embodiment, mutations can be introduced randomly along all or part of a 26443 or 46873 coding sequence, such as by saturation mutagenesis, and the resultant mutants can be screened for 26443 or 46873 biological activity to identify mutants that retain activity. Following mutagenesis of SEQ ID NO:1, SEQ ID NO:3, SEQ ID NO:4 or SEQ ID NO:6, the encoded protein can be expressed recombinantly and the activity of the protein can be determined.

As used herein, a "biologically active portion" of a 26443 or 46873 protein includes a fragment of a 26443 or 46873 protein that participates in an interaction between a 26443 or 46873 molecule and a non-26443 or -46873 molecule. Biologically active portions of a 26443 or 46873 protein include peptides comprising amino acid sequences sufficiently homologous to or derived from the amino acid sequence of the 26443 or 46873 protein, e.g., the amino acid sequence shown in SEQ ID NO:2 or SEQ ID NO:5, respectively, which include less amino acids than the full length 26443 or 46873 proteins, and exhibit at least one activity of a 26443 or 46873 protein. Typically, biologically active portions comprise a domain or motif with at least one activity of the 26443 or 46873 protein, e.g., asparaginase. A biologically active portion of a 26443 or 46873 protein can be a polypeptide that is, for example, 50, 100, 200 or more amino acids in length. Biologically active portions of a 26443 or 46873 protein can be used as targets for developing agents, which modulate a 26443- or 46873-mediated activity, e.g., asparaginase.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 26443 amino acid sequence of SEQ ID NO:2 having 125 amino acid residues, at least 167, preferably at least 209, more preferably at least 251, and even more preferably at least 293, 334, 376 or 418 amino acid residues are aligned; when aligning a second sequence to the 46873 amino acid sequence of SEQ ID NO:5 having 92 amino acid residues, at least 123, preferably at least 154, more preferably at least 185, and even more preferably at least 216, 246, 277 or 308 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if the molecule is within the sequence identity limits of a claim) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (CABIOS, 4:11–17 (1989)) which has been incorporated into the ALIGN program (version 2.0), using a PAM 120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403–10. BLAST nucleotide searches can be performed with the NBLAST program, score=100, wordlength=12 to obtain nucleotide sequences homologous to 26443 or 46873 nucleic acid molecules of the invention. BLAST protein searches can be performed with the XBLAST program, score=50, wordlength=3 to obtain amino acid sequences homologous to 26443 or 46873 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used "Misexpression or aberrant expression", as used herein, refers to a non-wild type pattern of gene expression, at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules of 26443 and 46873

In one aspect, the invention provides, an isolated or purified, nucleic acid molecule that encodes a 26443 or 46873 polypeptide described herein, e.g., a full-length 26443 or 46873 protein or a fragment thereof, e.g., a biologically active portion of a 26443 or 46873 protein. Also included is a nucleic acid fragment suitable for use as a hybridization probe, which can be used, e.g., to a identify a nucleic acid molecule encoding a polypeptide of the invention, 26443 or 46873 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of any of these nucleotide sequences. In one embodiment, the nucleic acid molecule includes sequences encoding the human 26443 protein (i.e., "the coding region", from nucleotides 91–1344 of SEQ ID NO:1), as well as 5' untranslated sequences (nucleotides 1–90 of SEQ ID NO:1) and 3' untranslated sequences (nucleotides 1345–1888 of SEQ ID NO:1). Alternatively, the nucleic acid molecule can include only the coding region of SEQ ID NO:1 (e.g., nucleotides 91–1344, corresponding to SEQ ID NO:3) and, e.g., no flanking sequences which normally accompany the subject sequence. In another embodiment, the nucleic acid molecule encodes a sequence corresponding to the mature protein from about amino acid 1 to amino acid 418 of SEQ ID NO:2.

In another embodiment, an isolated nucleic acid molecule of the invention includes the nucleotide sequence shown in SEQ ID NO:4, or a portion of any of these nucleotide sequences. In one embodiment, the nucleic acid molecule includes sequences encoding the human 46873 protein (i.e., "the coding region", from nucleotides 134–1057 of SEQ ID NO:4), as well as 5' untranslated sequences (nucleotides 1–133 of SEQ ID NO:4) and 3' untranslated sequences (nucleotides 1058–1358 of SEQ ID NO:4). Alternatively, the nucleic acid molecule can include only the coding region of SEQ ID NO:4 (e.g., nucleotides 134–1057, corresponding to SEQ ID NO:6) and, e.g., no flanking sequences which normally accompany the subject sequence. In another embodiment, the nucleic acid molecule encodes a sequence corresponding to the mature protein from about amino acid 1 to amino acid 308 of SEQ ID NO:5.

In another embodiment, an isolated nucleic acid molecule of the invention includes a nucleic acid molecule which is a complement of the nucleotide sequence shown in SEQ ID NO:1, SEQ ID NO:3, SEQ ID NO:4 or SEQ ID NO:6, or a portion of any of these nucleotide sequences. In other embodiments, the nucleic acid molecule of the invention is sufficiently complementary to the nucleotide sequence shown in SEQ ID NO:1, SEQ ID NO:3, SEQ ID NO:4 or SEQ ID NO:6, such that it can hybridize to the nucleotide sequence shown in SEQ ID NO:1, SEQ ID NO:3, SEQ ID NO:4 or SEQ ID NO:6, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1, SEQ ID NO:3, SEQ ID NO:4 or SEQ ID NO:6, or a portion, preferably of the same length, of any of these nucleotide sequences.

26443 or 46873 Nucleic Acid Fragments

A nucleic acid molecule of the invention can include only a portion of the nucleic acid sequence of SEQ ID NO:1, SEQ ID NO:3, SEQ ID NO:4 or SEQ ID NO:6. For example, such a nucleic acid molecule can include a fragment that can be used as a probe or primer or a fragment encoding a portion of a 26443 or 46873 protein, e.g., an immunogenic or biologically active portion of a 26443 or 46873 protein. A fragment can comprise nucleotides 202 to 1125 of SEQ ID NO:1, which encodes an asparaginase domain of human 26443, or nucleotides 134 to 1039 of SEQ ID NO:4, which also encodes an asparaginase domain of human 46873. The nucleotide sequence determined from the cloning of the 26443 or 46873 gene allows for the generation of probes and primers designed for use in identifying and/or cloning other 26443 or 46873 family members, or fragments thereof, as well as 26443 or 46873 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment that includes a nucleotide sequence encoding an amino acid fragment described herein. Nucleic acid fragments can encode a specific domain or site described herein or fragments thereof, particularly fragments thereof that are at least 200, preferably 300 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a nucleic acid fragment can include a sequence corresponding to an asparaginase domain.

In a preferred embodiment, the fragment is at least 200, 300, 350, 400, 450, 500, 550, 600, 650, 700, 750, 800, 850, 900, 950, or 1000 nucleotides in length.

26443 or 46873 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1, SEQ ID NO:3, SEQ ID NO:4 or SEQ ID NO:6, or of a naturally occurring allelic variant or mutant of SEQ ID NO:1, SEQ ID NO:3, SEQ ID NO:4 or SEQ ID NO:6.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes an asparaginase domain (corresponding to residues 38–345 of SEQ ID NO:2 or residues 1–302 of SEQ ID NO:5.

In another embodiment, a set of primers is provided, e.g., primers suitable for use in a PCR, which can be used to amplify a selected region of a 26443 or 46873 sequence. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying all or a portion of a domain or region described herein, e.g., any of the following regions, are provided an asparaginase domain corresponding to residues 38–345 of SEQ ID NO:2 or residues 1–302 of SEQ ID NO:5.

A nucleic acid fragment can encode an epitope bearing region of a polypeptide described herein.

A nucleic acid fragment encoding a "biologically active portion of a 26443 or 46873 polypeptide" can be prepared by isolating a portion of the nucleotide sequence of SEQ ID NO:1, SEQ ID NO:3, SEQ ID NO:4 or SEQ ID NO:6, which encodes a polypeptide having a 26443 or 46873 biological activity (e.g., the biological activities of the 26443 or 46873 proteins described herein), expressing the encoded portion of the 26443 or 46873 protein (e.g., by recombinant expression in vitro) and assessing the activity of the encoded portion of the 26443 or 46873 protein. For example, a nucleic acid fragment encoding a biologically active portion of 26443 or 46873 includes an asparaginase domain, e.g., amino acid residues 38 to 345 of SEQ ID NO:2 or amino acid residues I to 302 of SEQ ID NO:5. A nucleic acid fragment encoding a biologically active portion of a 26443 or 46873 polypeptide may comprise a nucleotide sequence that is greater than 300 or more nucleotides in length (e.g., greater than about 400 nucleotides in length).

In preferred embodiments, a nucleic acid fragment of 26443 includes a nucleotide sequence which is at least about 300, at least about 353 (e.g., 355, 375, 400), at least about 400 (e.g., 500, 600, 700, 800), at least about 457 (e.g., 460, 500, 600, 700), or more nucleotides in length and hybridizes under stringent hybridization conditions to a nucleic acid molecule of SEQ ID NO:1, or SEQ ID NO:3.

In a preferred embodiment, a nucleic acid fragment of 26443 includes a nucleotide sequence comprising nucleotides 183–842, 459–842, 1195–1244, or 1644–1888 of SEQ ID NO:1, or a portion thereof, wherein each fragment hybridizes under stringent hybridization conditions to a nucleic acid molecule of SEQ ID NO:1, or SEQ ID NO:3. In another preferred embodiment, a nucleic acid fragment of 26443 includes a nucleotide sequence comprising nucleotides 1–842 of SEQ ID NO:1, or a portion thereof, wherein each portion is about 183 or longer nucleotides and hybridizes under stringent hybridization conditions to a nucleic acid molecule of SEQ ID NO:1, or SEQ ID NO:3.

In a preferred embodiment, a nucleic acid fragment has a nucleotide sequence other than A1793006, AA262517, R89654, or C07777.

In preferred embodiments, a nucleic acid fragment of 46873 includes a nucleotide sequence which is at least about 300, 400, 500, 560 (e.g., 570, 580, 590, 600), at least about 662 (e.g., 665, 666, 667, 668, 670, 680, 690, 700), or more nucleotides in length and hybridizes under stringent hybridization conditions to a nucleic acid molecule of SEQ ID NO:4, or SEQ ID NO:6.

In a preferred embodiment, a nucleic acid fragment of 46873 includes a nucleotide sequence of SEQ ID NO:4 or 6, or a portion thereof; or a portion of the 46873 sequence comprising nucleotides 1–680, 1–686, 1–692 or 1–785 of SEQ ID NO:4, or a portion thereof, wherein each fragment hybridizes under stringent hybridization conditions to a nucleic acid molecule of SEQ ID NO:4, or SEQ ID NO:6.

In a preferred embodiment, a nucleic acid fragment has a nucleotide sequence other than AI879995, AI928914, AW131805, or AI978667.

26443 or 46873 Nucleic Acid Variants

The invention further encompasses nucleic acid molecules that differ from the nucleotide sequence shown in SEQ ID NO:1, SEQ ID NO:3, SEQ ID NO:4 or SEQ ID NO:6. Such differences can be due to degeneracy of the genetic code (and result in a nucleic acid that encodes the same 26443 or 46873 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2 or SEQ ID NO:5. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one colon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1, SEQ ID NO:3, SEQ ID NO:4 or SEQ ID NO:6, e.g., as follows: by at least one but less than 10, 20, 30, or 40 nucleotides; at least one but less than 2%, 5%, 10% or 20% of the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:2 or SEQ ID NO:5 or a fragment of those sequences. Nucleic acid molecules encoding such polypeptides can readily be identified as being able to hybridize under stringent conditions, to the nucleotide sequence shown in SEQ ID NO:1, SEQ ID NO:3, SEQ ID NO:4 or SEQ ID NO:6, or a fragment of the sequence. Nucleic acid molecules corresponding to orthologs, homologs, and allelic variants of the 26443 or 46873 cDNAs of the invention can further be isolated by mapping to the same chromosome or locus as the 26443 or 46873 gene.

Preferred variants include those that are correlated with asparaginase activity.

Allelic variants of 26443 or 46873, e.g., human 26443 or 46873, include both functional and non-functional proteins. Functional allelic variants are naturally occurring amino acid sequence variants of the 26443 or 46873 protein within a population that maintain the ability to function as an asparaginase. Functional allelic variants will typically contain only conservative substitution of one or more amino acids of SEQ ID NO:2 or SEQ ID NO:5, or substitution, deletion or insertion of non-critical residues in non-critical regions of the protein. Non-functional allelic variants are naturally-occurring amino acid sequence variants of the 26443 or 46873, e.g., human 26443 or 46873, protein within a population that do not have the ability to function as an asparaginase. Non-functional allelic variants will typically contain a non-conservative substitution, a deletion, or insertion, or premature truncation of the amino acid sequence of SEQ ID NO:2 or SEQ ID NO:5, or a substitution, insertion, or deletion in critical residues or critical regions of the protein.

Moreover, nucleic acid molecules encoding other 26443 or 46873 family members and, thus, which have a nucleotide sequence which differs from the 26443 or 46873 sequences of SEQ ID NO:1, SEQ ID NO:3, SEQ ID NO:4 or SEQ ID NO:6, are intended to be within the scope of the invention.

Antisense Nucleic Acid Molecules, Ribozymes and Modified 26443 or 46873 Nucleic Acid Molecules In another aspect, the invention features, an isolated nucleic acid molecule that is antisense to 26443 or 46873. An "antisense" nucleic acid can include a nucleotide sequence that is complementary to a "sense" nucleic acid encoding a protein, e.g., complementary to the coding strand of a double-stranded cDNA molecule or complementary to an mRNA sequence. The antisense nucleic acid can be complementary to an entire 26443 or 46873 coding strand, or to only a portion thereof (e.g., the coding region of human 26443 or 46873 corresponding to SEQ ID NO:3 or SEQ ID NO:6, respectively). In another embodiment, the antisense nucleic acid molecule is antisense to a "noncoding region" of the coding strand of a nucleotide sequence encoding 26443 or 46873 (e.g., the 5' or 3' untranslated regions).

An antisense nucleic acid can be designed such that it is complementary to the entire coding region of 26443 or 46873 mRNA, but more preferably is an oligonucleotide that is antisense to only a portion of the coding or noncoding region of 26443 or 46873 mRNA. For example, the antisense oligonucleotide can be complementary to the region surrounding the translation start site of 26443 or 46873 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine-substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 26443 or 46873 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. A ribozyme having specificity for a 26443- or 46873-encoding nucleic acid can include one or more sequences complementary to the nucleotide sequence of a 26443 or 46873 cDNA disclosed herein (i.e., SEQ ID NO:1, SEQ ID NO:3, SEQ ID NO:4 or SEQ ID NO:6), and a sequence having known catalytic sequence responsible for mRNA cleavage (see U.S. Pat. No. 5,093,246 or Haselhoff and Gerlach (1988) *Nature* 334:585–591). For example, a derivative of a Tetrahymena L-19 IVS RNA can be constructed in which the nucleotide sequence of the active site is complementary to the nucleotide sequence to be cleaved in a 26443- or 46873-encoding mRNA. See, e.g., Cech et al., U.S. Pat. No. 4,987,071; and Cech et al., U.S. Pat. No. 5,116,742. Alternatively, 26443 or 46873 mRNA can be used to select a catalytic RNA having a specific ribonuclease activity from a pool of RNA molecules. See, e.g., Bartel, D. and Szostak, J. W. (1993) *Science* 261: 1411–1418.

26443 or 46873 gene expression can be inhibited by targeting nucleotide sequences complementary to the regulatory region of the 26443 or 46873 (e.g., the 26443 or 46873 promoter and/or enhancers) to form triple helical structures that prevent transcription of the 26443 or 46873 genes in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 26443 or 46873 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of 26443 or 46873 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 26443 or 46873 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization-triggered cross-linking agent, transport agent, or hybridization-triggered cleavage agent).

The invention also includes molecular beacon oligonucleotide primer and probe molecules having at least one region that is complementary to a 26443 or 46873 nucleic acid of the invention. One complementary region has a fluorophore, and the other, a quencher, such that the molecular beacon is useful for quantitating the presence of the 26443 or 46873 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 26443 or 46873 Polypeptides

In another aspect, the invention features, an isolated 26443 or 46873 protein, or fragment, e.g., a biologically active portion, for use as immunogens or antigens to raise or test (or more generally to bind) anti-26443 or -46873 antibodies. 26443 or 46873 protein can be isolated from cells or tissue sources using standard protein purification techniques. 26443 or 46873 protein or fragments thereof can be produced by recombinant DNA techniques or synthesized chemically.

Polypeptides of the invention include those that arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when the polypeptide is expressed in a native cell, or in systems which result in the alteration or omission of post-translational modifications when expressed in a native cell, e.g., glycosylation or cleavage.

In a preferred embodiment, a 26443 or 46873 polypeptide has one or more of the following characteristics:

it has the ability to catalyze the hydrolysis of asparagine to aspartic acid and ammonia;

it has the ability to regulate the cellular levels of asparagine, aspartic acid and ammonia;

it has the ability to inhibit or decrease the availability of asparagine in tumors;

it has a molecular weight (e.g., deduced molecular weight), amino acid composition or other physical characteristic of a 26443 or a 46873 polypeptide, e.g., a polypeptide having a sequence shown in SEQ ID NO:2 or SEQ ID NO:5;

it has an overall sequence similarity of at least 60%, preferably at least 70%, more preferably at least 80, 90, or 95%, with a polypeptide of SEQ ID NO:2 or SEQ ID NO:5;

it has a asparaginase domain which is preferably about 60%, 70%, 80%, 90% or 95% homologous to amino acid residues 38–345 of SEQ ID NO:2 or residues 1–302 o SEQ ID NO:5; or it has at least 70%, preferably 80%, more preferably 90%, and most preferably 100% of the cysteines found in the amino acid sequence of the native protein.

In a preferred embodiment, the 26443 or 46873 protein, or fragment thereof, differs from the corresponding sequence in SEQ ID NO:2 or SEQ ID NO:5, respectively. In one embodiment, the protein differs by at least one, but by less than 15, 10 or 5 amino acid residues. In another, it differs from the corresponding sequence in SEQ ID NO:2 or SEQ ID NO:5 by at least one residue but less than 20%, 15%, 10% or 5% of the residues. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the asparaginase domain. In another preferred embodiment one or more differences are in the asparaginase domain.

Other embodiments include a protein that contain one or more changes in amino acid sequence, e.g., a change in an amino acid residue which is not essential for activity. Such 26443 or 46873 proteins differ in amino acid sequence from SEQ ID NO:2 or SEQ ID NO:5, respectively, yet retain biological activity.

In one embodiment, the protein includes an amino acid sequence that is at least about 60%, 65%, 70%, 75%, 80%, 85%, 90%, 95%, 98% or more homologous to SEQ ID NO:2 or SEQ ID NO:5.

A 26443 or 46873 protein or fragment is provided which varies from the sequence of SEQ ID NO:2 or SEQ ID NO:5, respectively, in non-essential regions (e.g., transmembrane domains) by at least one but by less than 15, 10 or 5 amino acid residues in the protein or fragment, but which does not differ from SEQ ID NO:2 or SEQ ID NO:5 in catalytic regions (e.g., the asparaginase domain). (If this comparison requires alignment the sequences should be aligned for maximum homology. "Looped" out sequences from deletions or insertions, or mismatches, are considered differences.) In some embodiments, the difference is at a non-essential residue or is a conservative substitution, while in others the difference is at an essential residue or is a non-conservative substitution.

In one embodiment, a biologically active portion of a 26443 or 46873 protein includes an asparaginase domain. Moreover, other biologically active portions, in which other regions of the protein are deleted, can be prepared by recombinant techniques and evaluated for one or more of the functional activities of a native 26443 or 46873 protein.

Particularly preferred 26443 or 46873 polypeptides of the present invention have an amino acid sequence substantially identical to the amino acid sequence of SEQ ID NO:2 or 5. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:2 or 5 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO: 1, 3, 4 or 6 are termed substantially identical.

26443 or 46873 Chimeric or Fusion Proteins

In another aspect, the invention provides 26443 or 46873 chimeric or fusion proteins. As used herein, a 26443 or 46873 "chimeric protein" or "fusion protein" includes a 26443 or 46873 polypeptide linked to a non-26443 or -46873 polypeptide. A "non-26443 or -46873 polypeptide" refers to a polypeptide having an amino acid sequence corresponding to a protein which is not substantially homologous to the 26443 or 46873 protein, e.g., a protein which is different from the 26443 or 46873 protein and which is derived from the same or a different organism. The 26443 or 46873 polypeptide of the fusion protein can correspond to all or a portion, e.g., a fragment described herein of a 26443 or 46873 amino acid sequence. In a preferred embodiment, a 26443 or 46873 fusion protein includes at least one (or two) biologically active portion of a 26443 or 46873 protein. The non-26443 or -46873 polypeptide can be fused to the N-terminus or C-terminus of the 26443 or 46873 polypeptide.

The fusion protein can include a moiety that has a high affinity for a ligand. For example, the fusion protein can be a GST-26443 or -46873 fusion protein in which the 26443 or 46873 sequences are fused to the C-terminus of the GST sequences. Such fusion proteins can facilitate the purification of recombinant 26443 or 46873. Alternatively, the fusion protein can be a 26443 or 46873 protein containing a heterologous signal sequence at its N-terminus. In certain host cells (e.g., mammalian host cells), expression and/or secretion of 26443 or 46873 can be increased through use of a heterologous signal sequence.

Fusion proteins can include all or a part of a serum protein, e.g., an IgG constant region, or human serum albumin.

The 26443 or 46873 fusion proteins of the invention can be incorporated into pharmaceutical compositions and administered to a subject in vivo. The 26443 or 46873 fusion proteins can be used to affect the bioavailability of a 26443 or 46873 substrate. 26443 or 46873 fusion proteins may be useful therapeutically for the treatment of disorders caused by, for example, (i) aberrant modification or mutation of a gene encoding a 26443 or 46873 protein; (ii) mis-regulation of the 26443 or 46873 gene; and (iii) aberrant post-translational modification of a 26443 or 46873 protein.

Moreover, the 26443- or 46873-fusion proteins of the invention can be used as immunogens to produce anti-26443 or -46873 antibodies in a subject, to purify 26443 or 46873 ligands and in screening assays to identify molecules that inhibit the interaction of 26443 or 46873 with a 26443 or 46873 substrate.

Expression vectors are commercially available that already encode a fusion moiety (e.g., a GST polypeptide). A 26443- or 46873-encoding nucleic acid can be cloned into such an expression vector such that the fusion moiety is linked in-frame to the 26443 or 46873 protein.

Variants of 26443 or 46873 Proteins

In another aspect, the invention also features a variant of a 26443 or 46873 polypeptide, e.g., which functions as an agonist (mimetics) or as an antagonist. Variants of the 26443 or 46873 proteins can be generated by mutagenesis, e.g., discrete point mutation, the insertion or deletion of sequences or the truncation of a 26443 or 46873 protein. An agonist of the 26443 or 46873 proteins can retain substantially the same, or a subset, of the biological activities of the naturally occurring form of a 26443 or 46873 protein. An antagonist of a 26443 or 46873 protein can inhibit one or more of the activities of the naturally occurring form of the 26443 or 46873 protein by, for example, competitively modulating a 26443- or 46873-mediated activity of a 26443 or 46873 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 26443 or 46873 protein.

Variants of a 26443 or 46873 protein can be identified by screening combinatorial libraries of mutants, e.g., truncation mutants, of a 26443 or 46873 protein for agonist or antagonist activity.

Libraries of fragments, e.g., N-terminal, C-terminal, or internal fragments, of a 26443 or 46873 protein coding sequence can be used to generate a variegated population of fragments for screening and subsequent selection of variants of a 26443 or 46873 protein.

Variants in which a cysteine residue is added or deleted or in which a residue that is glycosylated is added or deleted are particularly preferred.

Methods for screening gene products of combinatorial libraries made by point mutations or truncation, and for screening cDNA libraries for gene products having a selected property are known in the art. Recursive ensemble mutagenesis (REM), a new technique which enhances the frequency of functional mutants in the libraries, can be used in combination with the screening assays to identify 26443 or 46873 variants (Arkin and Yourvan (1992) *Proc. Natl. Acad. Sci. USA* 89:7811–7815; Delgrave et al. (1993) *Protein Engineering* 6(3):327–331).

Cell based assays can be exploited to analyze a variegated 26443 or 46873 library. For example, a library of expression vectors can be transfected into a cell line, e.g., a cell line, which ordinarily responds to 26443 or 46873 in a substrate-dependent manner. The transfected cells are then contacted with 26443 or 46873 and the effect of the expression of the mutant on the 26443 or 46873 substrate can be detected, e.g., by measuring fatty the amount of asparagine and/or aspartic acid and ammonia. Plasmid DNA can then be recovered from the cells that score for inhibition, or alternatively, potentiation of the mutant by the 26443 or 46873 substrate, and the individual clones further characterized.

In another aspect, the invention features a method of making a 26443 or 46873 polypeptide, e.g., a peptide having a non-wild type activity, e.g., an antagonist, agonist, or super agonist of a naturally occurring 26443 or 46873 polypeptide, e.g., a naturally occurring 26443 or 46873 polypeptide. The method includes: altering the sequence of a 26443 or 46873 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 26443 or 46873 polypeptide a biological activity of a naturally occurring 26443 or 46873 polypeptide. The method includes: altering the sequence, e.g., by substitution or deletion of one or more residues, of a 26443 or 46873 polypeptide, e.g., altering the sequence of a non-conserved region, or a domain or residue described herein, and testing the altered polypeptide for the desired activity.

Anti-26443 or -46873 Antibodies

In another aspect, the invention provides an anti-26443 or -46873 antibody. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

In a preferred embodiment, the antibody fails to bind an Fc receptor, e.g., it is an isotype which does not bind to an Fc receptor, or has been modified, e.g., by deletion or other mutation, such that it does not have a functional Fc receptor binding region.

A full-length 26443 or 46873 protein, or an antigenic peptide fragment of 26443 or 46873 can be used as an immunogen or can be used to identify anti-26443 or -46873 antibodies made with other immunogens, e.g., cells, membrane preparations, and the like. The antigenic peptide of 26443 or 46873 should include at least 8 amino acid residues of the amino acid sequence shown in SEQ ID NO:2 or SEQ ID NO:5, respectively, and encompasses an epitope of 26443 or 46873. Preferably, the antigenic peptide includes at least 10 amino acid residues, more preferably at least 15 amino acid residues, even more preferably at least 20 amino acid residues, and most preferably at least 30 amino acid residues.

Fragments of 26443 or 46873 which include, for example, residues 22–40, 48–65, 193–202, 203–230 or 345–361 of SEQ ID NO:2 or residues 12–26, 55–65 or 139–170 of SEQ ID NO:5, respectively, can be used to make, e.g., antibodies against hydrophilic regions of the 26443 or 46873 protein or used as immunogens or to characterize the specificity of an antibody. Similarly, a fragment of 26443 or 46873 which include, for example, residues 40–50, 75–90, 230–241 or 337–349 of SEQ ID NO:2 or residues 43–55, 90–105 or 138–170 of SEQ ID NO:5, respectively, can be used to make an antibody against a hydrophobic region of the 26443 or 46873 protein; a fragment of 26443 or 46873 which include residues 1–100, 50–150, 100–200, 150–250, 200–300, 250–350, 300–400 or 350–418 of SEQ ID NO:2 or residues 1–100, 50–150, 100–200, 150–250, 200–300 or 250–308 of SEQ ID NO:5, respectively, can be used to make an antibody against a non-transmembrane (i.e., matrix, cytosolic or lumen) region of the 26443 or 46873 protein; and a fragment of 26443 or 46873 which include residues 38–345 of SEQ ID NO:2 or residues 1–302 of SEQ ID NO:5, respectively, can be used to make an antibody against the asparaginase domain of the 26443 or 46873 protein.

Antibodies reactive with, or specific for, any of these regions, or other regions or domains described herein are provided.

Preferred epitopes encompassed by the antigenic peptide are regions of 26443 or 46873 are located on the surface of the protein, e.g., hydrophilic regions, as well as regions with high antigenicity. For example, an Emini surface probability analysis of the human 26443 or 46873 protein sequence can be used to indicate the regions that have a particularly high probability of being localized to the surface of the 26443 or 46873 protein and are thus likely to constitute surface residues useful for targeting antibody production. For example, residues 25–45, 55–65, 190–205 and 212–225 of the 26443 protein and residues 15–25 and 140–160 of the 46873 protein have a high probability of being localized on the surface of the respective proteins based on an Emini surface probability plot.

In a preferred embodiment, the antibody can bind to a 26443 or 46873 protein intracellularly. In another embodiment, the antibody binds to a 26443 or 46873 protein extracellularly.

In a preferred embodiment the antibody binds an epitope on any domain or region on 26443 or 46873 proteins described herein.

In preferred embodiments an antibody can be made by immunizing with purified 26443 or 46873 antigen, or a fragment thereof, e.g., a fragment described herein, membrane associated antigen, tissue, e.g., crude tissue preparations, whole cells, preferably living cells, lysed cells, or cell fractions, e.g., membrane fractions, cytoplasmic fractions.

Antibodies that bind only native 26443 or 46873 protein, only denatured or otherwise non-native 26443 or 46873 protein, or that bind both, are within the invention. Antibodies with linear or conformational epitopes are within the invention. Conformational epitopes can sometimes be determined by identifying antibodies that bind to native but not denatured 26443 or 46873 proteins.

Chimeric, humanized, but most preferably, completely human antibodies are desirable for applications which include repeated administration, e.g., therapeutic treatment (and some diagnostic applications) of human patients.

The anti-26443 or -46873 antibody can be a single-chain antibody. A single-chain antibody (scFV) may be engineered (see, for example, Colcher, D., et al. *Ann N Y Acad Sci Jun.* 30, 1999; 880:263–80; and Reiter, Y. *Clin Cancer Res February* 1996;2(2):245–52). The single-chain antibody can be dimerized or multimerized to generate multivalent antibodies having specificities for different epitopes of the same target 26443 or 46873 protein.

An anti-26443 or -46873 antibody (e.g., monoclonal antibody) can be used to isolate 26443 or 46873 by standard techniques, such as affinity chromatography or immunoprecipitation. Moreover, an anti-26443 or -46873 antibody can be used to detect 26443 or 46873 protein (e.g., in a cellular lysate or cell supernatant) in order to evaluate the abundance and pattern of expression of the protein. Anti-26443 or -46873 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes a nucleic acid that encodes an anti-26443 or -46873 antibody, e.g., an anti-26443 or -46873 antibody described herein. Also included are vectors which include the nucleic acid and cells transformed with the nucleic acid, particularly cells which are useful for producing an antibody, e.g., mammalian cells, e.g. CHO or lymphatic cells.

The invention also includes cell lines, e.g., hybridomas, which make an anti-26443 or -46873 antibody, e.g., and antibody described herein, and method of using said cells to make an anti-26443 or -46873 antibody.

26443 and 46873 Recombinant Expression Vectors, Host Cells and Genetically Engineered Cells In another aspect, the invention includes vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 26443 or 46873 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 26443 or 46873 proteins, mutant forms of 26443 or 46873 proteins, fusion proteins, and the like).

The recombinant expression vectors of the invention can be designed for expression of 26443 or 46873 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 26443 or 46873 activity assays, (e.g., direct assays or competitive assays described in detail below), or to generate antibodies specific for 26443 or 46873 proteins. In a preferred embodiment, a fusion protein expressed in a retroviral expression vector of the present invention can be used to infect bone marrow cells that are subsequently transplanted into irradiated recipients. The pathology of the subject recipient is then examined after sufficient time has passed (e.g., six (6) weeks).

One strategy used to maximize recombinant protein expression in *E. coli* is to express the protein in a host strain with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

The 26443 or 46873 expression vector can be a yeast expression vector, a vector for expression in insect cells, e.g., a baculovirus expression vector, or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No.4,873, 316 and European Application Publication No. 264,166).

Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes, see Weintraub, H. et al., Antisense RNA as a molecular tool for genetic analysis, *Reviews—Trends in Genetics,* Vol. 1(1) 1986.

Another aspect the invention provides a host cell which includes a nucleic acid molecule described herein, e.g., a 26443 or 46873 nucleic acid molecule within a recombinant expression vector or a 26443 or 46873 nucleic acid molecule containing sequences which allow it to homologously recombine into a specific site of the host cell's genome. The terms "host cell" and "recombinant host cell" are used interchangeably herein. Such terms refer not only to the particular subject cell, but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 26443 or 46873 protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 26443 or 46873 protein. Accordingly, the invention further provides methods for producing a 26443 or 46873 protein using the host cells of the invention. In one embodiment, the method includes culturing the host cell of the invention (into which a recombinant expression vector encoding a 26443 or 46873 protein has been introduced) in a suitable medium such that a 26443 or 46873 protein is produced. In another embodiment, the method further includes isolating a 26443 or 46873 protein from the medium or the host cell.

In another aspect, the invention features, a cell or purified preparation of cells that include a 26443 or 46873 transgene, or which otherwise misexpress 26443 or 46873. The cell preparation can consist of human or non-human cells, e.g., rodent cells, e.g., mouse or rat cells, rabbit cells, or pig cells. In preferred embodiments, the cell or cells include a 26443 or 46873 transgene, e.g., a heterologous form of a 26443 or 46873, e.g., a gene derived from humans (in the case of a non-human cell). The 26443 or 46873 transgene can be misexpressed, e.g., overexpressed or underexpressed. In other preferred embodiments, the cell or cells include a gene that misexpresses an endogenous 26443 or 46873, e.g., a gene for which expression is disrupted, e.g., a knockout. Such cells can serve as a model for studying disorders that are related to mutated or misexpressed 26443 or 46873 alleles or for use in drug screening.

In another aspect, the invention features, a human cell, e.g., a tumor cell, transformed with a nucleic acid that encodes a subject 26443 or 46873 polypeptide.

Also provided are cells, e.g., human cells, e.g., human hematopoietic or fibroblast cells, in which an endogenous 26443 or 46873 is under the control of a regulatory sequence that does not normally control the expression of the endogenous 26443 or 46873 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 26443 or 46873 gene. For example, an endogenous 26443 or 46873 gene, e.g., a gene that is "transcriptionally silent", e.g., not normally expressed, or expressed only at very low levels, may be activated by inserting a regulatory element which is capable of promoting the expression of a normally expressed gene product in that cell. Techniques, such as targeted homologous recombination, can be used to insert the heterologous DNA as described in, e.g., Chappel, U.S. Pat. No. 5,272,071; WO 91/06667, published in May 16, 1991.

26443 and 46873 Transgenic Animals

The invention provides non-human transgenic animals. Such animals are useful for studying the function and/or activity of a 26443 or 46873 protein and for identifying and/or evaluating modulators of 26443 or 46873 activity. As used herein, a "transgenic animal" is a non-human animal, preferably a mammal, more preferably a rodent such as a rat or mouse, in which one or more of the cells of the animal include a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 26443 or 46873 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 26443 or 46873 protein to particular cells. A transgenic founder animal can be identified based upon the presence of a 26443 or 46873 transgene in its genome and/or expression of 26443 or 46873 mRNA in tissues or cells of the animals. A transgenic founder animal can then be used to breed additional animals carrying the transgene. Moreover, transgenic animals carrying a transgene encoding a 26443 or 46873 protein can further be bred to other transgenic animals carrying other transgenes.

26443 or 46873 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses of 26443 and 46873

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 26443 or 46873 protein (e.g., via a recombinant expression vector in a host cell in gene therapy applications), to detect a 26443 or 46873 mRNA (e.g., in a biological sample) or a genetic alteration in a 26443 or 46873 gene, and to modulate 26443 or 46873 activity, as described further below. The 26443 or 46873 proteins can be used to treat disorders characterized by insufficient or excessive production of a 26443 or 46873 substrate or production of 26443 or 46873 inhibitors. In addition, the 26443 or 46873 proteins can be used to screen for naturally occurring 26443 or 46873 substrates, to screen for drugs or compounds which modulate 26443 or 46873 activity, as well as to treat disorders characterized by insufficient or excessive production of 26443 or 46873 protein or production of 26443 or 46873 protein forms which have decreased, aberrant or unwanted activity compared to 26443 or 46873 wild type protein (e.g., altered cellular levels of asparagine and/or aspartic acid and ammonia). Moreover, the anti-26443 or -46873 antibodies of the invention can be used to detect and isolate 26443 or 46873 proteins, regulate the bioavailability of 26443 or 46873 proteins, and modulate 26443 or 46873 activity.

A method of evaluating a compound for the ability to interact with, e.g., bind, a subject 26443 or 46873 polypeptide is provided. The method includes: contacting the compound with the subject 26443 or 46873 polypeptide; and evaluating the ability of the compound to interact with, e.g., to bind or form a complex with, the subject 26443 or 46873 polypeptide. This method can be performed in vitro, e.g., in a cell free system, or in vivo, e.g., in a two-hybrid interaction trap assay. This method can be used to identify naturally occurring molecules that interact with a subject 26443 or 46873 polypeptide. It can also be used to find natural or synthetic inhibitors of a subject 26443 or 46873 polypeptide. Screening methods are discussed in more detail below.

26443 and 46873 Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 26443 or 46873 proteins, have a stimulatory or inhibitory effect on, for example, 26443 or 46873 expression or 26443 or 46873 activity, or have a stimulatory or inhibitory effect on, for example, the expression or activity of a 26443 or 46873 substrate. Compounds thus identified can be used to modulate the activity of target gene products (e.g., 26443 or 46873 genes) in a therapeutic protocol, to elaborate the biological function of the target gene product, or to identify compounds that disrupt normal target gene interactions.

In one embodiment, the invention provides assays for screening candidate or test compounds that are substrates of a 26443 or 46873 protein or polypeptide or a biologically active portion thereof. In another embodiment, the invention provides assays for screening candidate or test compounds that bind to or modulate the activity of a 26443 or 46873 protein or polypeptide or a biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al. *J. Med. Chem.* 1994, 37: 2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner USP '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra).

In one embodiment, an assay is a cell-based assay in which a cell that expresses a 26443 or 46873 protein or biologically active portion thereof is contacted with a test compound, and the ability of the test compound to modulate 26443 or 46873 activity is determined. Determining the ability of the test compound to modulate 26443 or 46873 activity can be accomplished by monitoring, for example, cellular asparagine levels. The cell, for example, can be of mammalian origin, e.g., a tumor cell.

The ability of the test compound to modulate 26443 or 46873 binding to a compound, e.g., a 26443 or 46873 substrate, or to bind to 26443 or 46873 can also be evaluated. This can be accomplished, for example, by coupling the compound, e.g., the substrate, with a radioisotope or enzymatic label such that binding of the compound, e.g., the substrate, to 26443 or 46873 can be determined by detecting the labeled compound, e.g., substrate, in a complex. Alternatively, 26443 or 46873 could be coupled with a radioisotope or enzymatic label to monitor the ability of a test compound to modulate 26443 or 46873 binding to a 26443 or 46873 substrate in a complex. For example, compounds (e.g., 26443 or 46873 substrates) can be labeled with $^{125}$I, $^{35}$S, $^{14}$C, or $^3$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 26443 or 46873 substrate) to interact with 26443 or 46873 with or without the labeling of any of the interactants can be evaluated. For example, a microphysiometer can be used to detect the interaction of a compound with 26443 or 46873 without the labeling of either the compound or the 26443 or 46873. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 26443 or 46873.

In yet another embodiment, a cell-free assay is provided in which a 26443 or 46873 protein or biologically active portion thereof is contacted with a test compound and the ability of the test compound to bind to the 26443 or 46873 protein or biologically active portion thereof is evaluated. Preferred biologically active portions of the 26443 or 46873 proteins to be used in assays of the present invention include fragments that participate in interactions with non-26443 or -46873 molecules, e.g., fragments with high surface probability scores.

Soluble and/or membrane-bound forms of isolated proteins (e.g., 26443 or 46873 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that it's emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 26443 or 46873 protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIA-core). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 26443 or 46873, an anti-26443 or -46873 antibody or its target molecule to facilitate separation of complexed from uncomplexed forms of one or both of the proteins, as well as to accommodate automation of the assay. Binding of a test compound to a 26443 or 46873 protein, or interaction of a 26443 or 46873 protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase-26443 or -46873 fusion proteins or glutathione-S-transferase-target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 26443 or 46873 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 26443 or 46873 binding or activity determined using standard techniques.

Other techniques for immobilizing either a 26443 or 46873 protein or a target molecule on matrices include using conjugation of biotin and streptavidin. Biotinylated 26443 or 46873 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 26443 or 46873 protein or target molecules but which do not interfere with binding of the 26443 or 46873 protein to its target molecule. Such antibodies can be derivatized to the wells of the plate, and unbound target or 26443 or 46873 protein trapped in the wells by antibody conjugation. Methods for detecting such complexes, in addition to those described above for the GST-immobilized complexes, include immunodetection of complexes using antibodies reactive with the 26443 or 46873 protein or target molecule, as well as enzyme-linked assays which rely on detecting an enzymatic activity associated with the 26443 or 46873 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., *Trends Biochem Sci August* 1993;18(8):284–7); chromatography (gel filtration chromatography, ion-exchange chromatography); electrophoresis (see, e.g., Ausubel, F. et al., eds. Current Protocols in Molecular Biology 1999, J. Wiley: N.Y.); and immunoprecipitation (see, for example, Ausubel, F. et al., eds. Current Protocols in Molecular Biology 1999, J. Wiley: N.Y.). Such resins and chromatographic techniques are known to one skilled in the art (see, e.g., Heegaard, N. H., *J Mol Recognit* 1998 Winter;11(1–6):141–8; Hage, D. S., and Tweed, S. A. *J Chromatogr B Biomed Sci Appl* Oct. 10, 1997; 699(1–2):499–525). Further, fluorescence energy transfer may also be conveniently utilized, as described herein, to detect binding without further purification of the complex from solution.

In a preferred embodiment, the assay includes contacting the 26443 or 46873 protein or biologically active portion thereof with a known compound which binds 26443 or 46873 to form an assay mixture, contacting the assay mixture with a test compound, and determining the ability of the test compound to interact with a 26443 or 46873 protein, wherein determining the ability of the test compound to interact with a 26443 or 46873 protein includes determining the ability of the test compound to preferentially bind to 26443 or 46873 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 26443 or 46873 genes herein identified. In an alternative embodiment, the invention provides methods for determining the ability of the test compound to modulate the activity of a 26443 or 46873 protein through modulation of the activity of a downstream effector of a 26443 or 46873 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 26443 or 46873 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 26443 or 46873 ("26443- or 46873-binding proteins" or "26443- or 46873-bp") and are involved in 26443 or 46873 activity. Such 26443- or 46873-bps can be activators or inhibitors of signals by the 26443 or 46873 proteins or 26443 or 46873 targets as, for example, downstream elements of a 26443- or 46873-mediated signaling pathway.

The two-hybrid system is based on the modular nature of most transcription factors, which consist of separable DNA-binding and activation domains. Briefly, the assay utilizes two different DNA constructs. In one construct, the gene that codes for a 26443 or 46873 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively, the 26443 or 46873 protein can be the fused to the activator domain.) If the "bait" and the "prey" proteins are able to interact, in vivo, forming a 26443- or 46873-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein that interacts with the 26443 or 46873 protein.

In another embodiment, modulators of 26443 or 46873 expression are identified. For example, a cell or cell free mixture is contacted with a candidate compound and the expression of 26443 or 46873 mRNA or protein evaluated relative to the level of expression of 26443 or 46873 mRNA or protein in the absence of the candidate compound. When expression of 26443 or 46873 mRNA or protein is greater in the presence of the candidate compound than in its absence, the candidate compound is identified as a stimulator of 26443 or 46873 mRNA or protein expression. Alternatively, when expression of 26443 or 46873 mRNA or protein is less (e.g., statistically significantly less) in the presence of the candidate compound than in its absence, the candidate compound is identified as an inhibitor of 26443 or 46873 mRNA or protein expression. The level of 26443 or 46873 mRNA or protein expression can be determined by methods described herein for detecting 26443 or 46873 mRNA or protein.

In another aspect, the invention pertains to a combination of two or more of the assays described herein. For example, a modulating agent can be identified using a cell-based or a cell free assay, and the ability of the agent to modulate the activity of a 26443 or 46873 protein can be confirmed in vivo, e.g., in an animal such as an animal model for aberrant fatty acid oxidation.

This invention further pertains to novel agents identified by the above-described screening assays. Accordingly, it is within the scope of this invention to further use an agent identified as described herein (e.g., a 26443 or 46873 modulating agent, an antisense 26443 or 46873 nucleic acid molecule, a 26443- or 46873-specific antibody, or a 26443- or 46873-binding partner) in an appropriate animal model to determine the efficacy, toxicity, side effects, or mechanism of action, of treatment with such an agent. Furthermore, novel agents identified by the above-described screening assays can be used for treatments as described herein.

26443 and 46873 Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 26443 or 46873 with a disease; (ii) identify an individual from a minute biological sample (tissue typing); and (iii) aid in forensic identification of a biological sample. These applications are described in the subsections below.

26443 and 46873 Chromosome Mapping

The 26443 or 46873 nucleotide sequences or portions thereof can be used to map the location of the 26443 or 46873 genes on a chromosome. This process is called chromosome mapping. Chromosome mapping is useful in correlating the 26443 or 46873 sequences with genes associated with disease.

Briefly, 26443 or 46873 genes can be mapped to chromosomes by preparing PCR primers (preferably 15–25 bp in length) from the 26443 or 46873 nucleotide sequences. These primers can then be used for PCR screening of somatic cell hybrids containing individual human chromosomes. Only those hybrids containing the human gene corresponding to the 26443 or 46873 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919–924).

Other mapping strategies, e.g., in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries can be used to map 26443 or 46873 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to non-coding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the 26443 or 46873 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

26443 and 46873 Tissue Typing 26443 or 46873 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 26443 or 46873 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the non-coding regions. Each of the sequences described herein can, to some degree, be used as a standard against which DNA from an individual can be compared for identification purposes. Because greater numbers of polymorphisms occur in the non-coding regions, fewer sequences are necessary to differentiate individuals. The non-coding sequences of SEQ ID NO: 1 or SEQ ID NO:4 can provide positive individual identification with a panel of perhaps 10 to 1,000 primers which each yield a non-coding amplified sequence of 100 bases. If predicted coding sequences, such as those in SEQ ID NO:3 or SEQ ID NO:6 are used, a more appropriate number of primers for positive individual identification would be 500–2,000.

If a panel of reagents from 26443 or 46873 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 26443 or 46873 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to non-coding regions of SEQ ID NO: 1 or SEQ ID NO:4 (e.g., fragments derived from the non-coding regions of SEQ ID NO: 1 or SEQ ID NO:4 having a length of at least 20 bases, preferably at least 30 bases) are particularly appropriate for this use.

The 26443 or 46873 nucleotide sequences described herein can further be used to provide polynucleotide reagents, e.g., labeled or labelable probes which can be used in, for example, an in situ hybridization technique, to identify a specific tissue, e.g., a tissue containing organelles having asparaginase. This can be very useful in cases where a forensic pathologist is presented with a tissue of unknown origin. Panels of such 26443 or 46873 probes can be used to identify tissue by species and/or by organ type.

In a similar fashion, these reagents, e.g., 26443 or 46873 primers or probes can be used to screen tissue culture for contamination (i.e., screen for the presence of a mixture of different types of cells in a culture).

Predictive Medicine of 26443 and 46873

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene that encodes asparaginase.

Such disorders include, e.g., a disorder associated with the misexpression of an asparaginase; or a metabolic disorder, e.g., a disorder involving inappropriate cellular asparagine levels.

The method includes one or more of the following:

detecting, in a tissue of the subject, the presence or absence of a mutation which affects the expression of the 26443 or 46873 gene, or detecting the presence or absence of a mutation in a region which controls the expression of the gene, e.g., a mutation in the 5' control region;

detecting, in a tissue of the subject, the presence or absence of a mutation which alters the structure of the 26443 or 46873 gene;

detecting, in a tissue of the subject, the misexpression of the 26443 or 46873 gene, at the mRNA level, e.g., detecting a non-wild type level of a mRNA;

detecting, in a tissue of the subject, the misexpression of the gene, at the protein level, e.g., detecting a non-wild type level of a 26443 or 46873 polypeptide.

In preferred embodiments the method includes: ascertaining the existence of at least one of: a deletion of one or more nucleotides from the 26443 or 46873 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO: 1 or 3 or naturally occurring mutants thereof, or 5' or 3' flanking sequences naturally associated with the 26443 or 46873 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 26443 or 46873 gene; the presence of a non-wild type splicing pattern of a messenger RNA transcript of the gene; or a non-wild type level of 26443 or 46873.

Methods of the invention can be used prenatally or to determine if a subject's offspring will be at risk for a disorder.

In preferred embodiments the method includes determining the structure of a 26443 or 46873 gene, an abnormal structure being indicative of risk for the disorder.

In preferred embodiments the method includes contacting a sample form the subject with an antibody to the 26443 or 46873 protein or a nucleic acid, which hybridizes specifically with the gene. These and other embodiments are discussed below.

Diagnostic and Prognostic Assays of 26443 and 46873

Diagnostic and prognostic assays of the invention include method for assessing the expression level of 26443 or 46873 molecules and for identifying variations and mutations in the sequence of 26443 or 46873 molecules.

Expression Monitoring and Profiling:

The presence, level, or absence of 26443 or 46873 protein or nucleic acid in a biological sample can be evaluated by obtaining a biological sample from a test subject and contacting the biological sample with a compound or an agent capable of detecting 26443 or 46873 protein or nucleic acid (e.g., mRNA, genomic DNA) that encodes 26443 or 46873 protein such that the presence of 26443 or 46873 protein or nucleic acid is detected in the biological sample. The term "biological sample" includes tissues, cells and biological fluids isolated from a subject, as well as tissues, cells and fluids present within a subject. A preferred biological sample is serum. The level of expression of the 26443 or 46873 gene can be measured in a number of ways, including, but not limited to: measuring the mRNA encoded by the 26443 or 46873 gene; measuring the amount of protein encoded by the 26443 or 46873 gene; or measuring the activity of the protein encoded by the 26443 or 46873 gene.

The level of mRNA corresponding to the 26443 or 46873 gene in a cell can be determined by both in situ and in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 26443 or 46873 nucleic acid, such as the nucleic acid of SEQ ID NO: 1, or a portion thereof, such as an oligonucleotide of at least 7, 15, 30, 50, 100, 250 or 500 nucleotides in length and sufficient to specifically hybridize under stringent conditions to 26443 or 46873 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 26443 or 46873 gene.

The level of mRNA in a sample that is encoded by one of 26443 or 46873 can be evaluated with nucleic acid amplification, e.g., by RT-PCR (Mullis (1987) U.S. Pat. No. 4,683,202), ligase chain reaction (Barany (1991) *Proc. Natl. Acad. Sci. USA* 88:189–193), self sustained sequence replication (Guatelli et al., (1990) *Proc. Natl. Acad. Sci. USA* 87:1874–1878), transcriptional amplification system (Kwoh et al., (1989), *Proc. Natl. Acad. Sci. USA* 86:1173–1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 26443 or 46873 gene being analyzed.

In another embodiment, the methods further contacting a control sample with a compound or agent capable of detecting 26443 or 46873 mRNA, or genomic DNA, and comparing the presence of 26443 or 46873 mRNA or genomic DNA in the control sample with the presence of 26443 or 46873 mRNA or genomic DNA in the test sample. In still another embodiment, serial analysis of gene expression, as described in U.S. Pat. No. 5,695,937, is used to detect 26443 or 46873 transcript levels.

A variety of methods can be used to determine the level of protein encoded by 26443 or 46873. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 26443 or 46873 protein in a biological sample in vitro as well as in vivo. In vitro techniques for detection of 26443 or 46873 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 26443 or 46873 proteins include introducing into a subject a labeled anti-26443 or -46873 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-26443 or -46873 antibody positioned on an antibody array (as described below). The sample can be detected, e.g., with avidin coupled to a fluorescent label.

In another embodiment, the methods further include contacting the control sample with a compound or agent capable of detecting 26443 or 46873 proteins, and comparing the presence of 26443 or 46873 proteins in the control sample with the presence of 26443 or 46873 proteins in the test sample.

The invention also includes kits for detecting the presence of 26443 or 46873 in a biological sample. For example, the kit can include a compound or agent capable of detecting 26443 or 46873 protein or mRNA in a biological sample; and a standard. The compound or agent can be packaged in a suitable container. The kit can further comprise instructions for using the kit to detect 26443 or 46873 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein-stabilizing agent. The kit can also includes components necessary for detecting the detectable agent (e.g., an enzyme or a substrate). The kit can also contain a control sample or a series of control samples that can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with mis-expressed or aberrant or unwanted 26443 or 46873 expression or activity. As used herein, the term "unwanted" includes an unwanted phenomenon involved in a biological response such as pain or deregulated cell proliferation.

In one embodiment, a disease or disorder associated with aberrant or unwanted 26443 or 46873 expression or activity is identified. A test sample is obtained from a subject and 26443 or 46873 protein or nucleic acid (e.g., mRNA or genomic DNA) is evaluated, wherein the level, e.g., the presence or absence, of 26443 or 46873 protein or nucleic acid is diagnostic for a subject having or at risk of developing a disease or disorder associated with aberrant or unwanted 26443 or 46873 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 26443 or 46873 expression or activity. For example, such methods can be used to determine whether a subject can be effectively treated with an agent for a disorder involving aberrant or unwanted 26443 or 46873 expression or activity.

In another aspect, the invention features a computer medium having a plurality of digitally encoded data records. Each data record includes a value representing the level of expression of 26443 or 46873 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 26443 or 46873 (e.g., other genes associated with a 26443- or 46873-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 26443 or 46873 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a disorder involving aberrant or unwanted 26443 or 46873 expression or activity in a subject. The method can be used to monitor a treatment for a disorder involving aberrant or unwanted 26443 or 46873 expression or activity in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 26443 or 46873 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 26443 or 46873 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 26443 or 46873 expression.

26443 and 46873 Arrays and Uses Thereof

In another aspect, the invention features an array that includes a substrate having a plurality of addresses. At least one address of the plurality includes a capture probe that binds specifically to a 26443 or 46873 molecule (e.g., a 26443 or 46873 nucleic acid or a 26443 or 46873 polypeptide). The array can have a density of at least than 10, 50, 100, 200, 500, 1,000, 2,000, or 10,000 or more addresses/$cm^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 26443 or 46873 nucleic acid, e.g., the sense or anti-sense strand. In one preferred embodiment, a subset of addresses of the plurality of addresses has a nucleic acid capture probe for 26443 or 46873. Each address of the subset can include a capture probe that hybridizes to a different region of a 26443 or 46873 nucleic acid. In another preferred embodiment, addresses of the subset include a capture probe for a 26443 or 46873 nucleic acid. Each address of the subset is unique, overlapping, and complementary to a different variant of 26443 or 46873 (e.g., an allelic variant, or all possible hypothetical variants). The array can be used to sequence 26443 or 46873 by hybridization (see, e.g., U.S. Pat. No. 5,695,940).

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 26443 or 46873 polypeptide or fragment thereof. The polypeptide can be a naturally occurring interaction partner of 26443 or 46873 polypeptide. Preferably, the polypeptide is an antibody, e.g., an antibody described herein (see "Anti-26443 or -46873 Antibodies," above), such as a monoclonal antibody or a single-chain antibody.

In another aspect, the invention features a method of analyzing the expression of 26443 or 46873. The method includes providing an array as described above; contacting the array with a sample and detecting binding of a 26443 or 46873-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 26443 or 46873. If a sufficient number of diverse samples is analyzed, clustering (e.g., hierarchical clustering, k-means clustering, Bayesian clustering and the like) can be used to identify other genes which are co-regulated with 26443 or 46873. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 26443 or 46873 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 26443- or 46873-associated disease or disorder; and processes, such as a cellular transformation associated with a 26443- or 46873-associated disease or disorder. The method can also evaluate the treatment and/or progression of a 26443- or 46873-associated disease or disorder The array is also useful for ascertaining differential expression patterns of one or more genes in normal and abnormal cells. This provides a battery of genes (e.g., including 26443 or 46873) that could serve as a molecular target for diagnosis or therapeutic intervention.

In another aspect, the invention features an array having a plurality of addresses. Each address of the plurality includes a unique polypeptide. At least one address of the plurality has disposed thereon a 26443 or 46873 polypeptide or fragment thereof. Methods of producing polypeptide arrays are described in the art, e.g., in De Wildt et al. (2000). *Nature Biotech*. 18, 989–994; Lueking et al. (1999). *Anal. Biochem*. 270, 103–111; Ge, H. (2000). *Nucleic Acids Res*. 28, e3, I–VII; MacBeath, G., and Schreiber, S. L. (2000). *Science* 289, 1760–1763; and WO 99/51773A1. In a preferred embodiment, each addresses of the plurality has disposed thereon a polypeptide at least 60, 70, 80, 85, 90, 95 or 99% identical to a 26443 or 46873 polypeptide or fragment thereof. For example, multiple variants of a 26443 or 46873 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 26443 or 46873 binding compound, e.g., an antibody in a sample from a subject with specificity for a 26443 or 46873 polypeptide or the presence of a 26443- or 46873-binding protein or ligand.

The array is also useful for ascertaining the effect of the expression of a gene on the expression of other genes in the same cell or in different cells (e.g., ascertaining the effect of 26443 or 46873 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 26443 or 46873 or from a cell or subject in which a 26443 or 46873 mediated response has been elicited, e.g., by contact of the cell with 26443 or 46873 nucleic acid or protein, or administration to the cell or subject 26443 or 46873 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 26443 or 46873 (or does not express as highly as in the case of the 26443 or 46873 positive plurality of capture probes) or from a cell or subject which in which a 26443- or 46873-mediated response has not been elicited (or has been elicited to a lesser extent than in the first sample); contacting the array with one or more inquiry probes (which is preferably other than a 26443 or 46873 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 26443 or 46873 or from a cell or subject in which a 26443- or 46873-mediated response has been elicited, e.g., by contact of the cell with 26443 or 46873 nucleic acid or protein, or administration to the cell or subject 26443 or 46873 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 26443 or 46873 (or does not express as highly as in the case of the 26443 or 46873 positive plurality of capture probes) or from a cell or subject which in which a 26443 or 46873 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 26443 or 46873, e.g., analyzing structure, function, or relatedness to other nucleic acid or amino acid sequences. The method includes: providing a 26443 or 46873 nucleic acid or amino acid sequence; comparing the 26443 or 46873 sequence with one or more preferably a plurality of sequences from a collection of sequences, e.g., a nucleic acid or protein sequence database; to thereby analyze 26443 or 46873.

Detection of 26443 and 46873 Variations or Mutations

The methods of the invention can also be used to detect genetic alterations in a 26443 or 46873 gene, thereby determining if a subject with the altered gene is at risk for a disorder characterized by mis-regulation in 26443 or 46873 protein activity or nucleic acid expression, such as a disorder involving aberrant or unwanted 26443 or 46873 expression or activity. In preferred embodiments, the methods include detecting, in a sample from the subject, the presence or absence of a genetic alteration characterized by at least one of an alteration affecting the integrity of a gene encoding a 26443 or 46873 proteins, or the mis-expression of the 26443 or 46873 genes. For example, such genetic alterations can be detected by ascertaining the existence of at least one of 1) a deletion of one or more nucleotides from a 26443 or 46873 gene; 2) an addition of one or more nucleotides to a 26443 or 46873 gene; 3) a substitution of one or more nucleotides of a 26443 or 46873 gene, 4) a chromosomal rearrangement of a 26443 or 46873 gene; 5) an alteration in the level of a messenger RNA transcript of a 26443 or 46873 gene, 6) aberrant modification of a 26443 or 46873 gene, such as of the methylation pattern of the genomic DNA, 7) the presence of a non-wild type splicing pattern of a messenger RNA transcript of a 26443 or 46873 gene, 8) a non-wild type level of a 26443 or 46873 protein, 9) allelic loss of a 26443 or 46873 gene, and 10) inappropriate post-translational modification of a 26443 or 46873 protein.

An alteration can be detected without a probe/primer in a polymerase chain reaction, such as anchor PCR or RACE-PCR, or, alternatively, in a ligation chain reaction (LCR), the latter of which can be particularly useful for detecting point mutations in the 26443 or 46873 gene. This method can include the steps of collecting a sample of cells from a subject, isolating nucleic acid (e.g., genomic, mRNA or both) from the sample, contacting the nucleic acid sample with one or more primers which specifically hybridize to a 26443 or 46873 gene under conditions such that hybridization and amplification of the 26443 or 46873 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 26443 or 46873 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No.5,498,531) can be used to score for the presence of specific mutations by development or loss of a ribozyme cleavage site.

In other embodiments, genetic mutations in 26443 or 46873 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 26443 or a 46873 nucleic acid or a putative variant (e.g., allelic variant) thereof. A probe can have one or more mismatches to a region of a 26443 or 46873 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 26443 or 46873 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 26443 or 46873 gene and detect mutations by comparing the sequence of the sample 26443 or 46873 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 26443 or 46873 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 26443 or 46873 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 26443 or 46873 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control 26443 or 46873 nucleic acids will be denatured and allowed to renature. The secondary structure of single-stranded nucleic acids varies according to the sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 26443 or 46873 nucleic acid.

In a preferred embodiment the set includes a first and a second oligonucleotide. The first and second oligonucleotide can hybridize to the same or to different locations of SEQ ID NO: 1, 3, 4 or 6 or the complement of SEQ ID NO: 1, 3, 4 or 6. Different locations can be different but overlapping or or non-overlapping on the same strand. The first and second oligonucleotide can hybridize to sites on the same or on different strands.

The set can be useful, e.g., for identifying SNP's, or identifying specific alleles of 26443 or 46873. In a preferred embodiment, each oligonucleotide of the set has a different nucleotide at an interrogation position. In one embodiment, the set includes two oligonucleotides, each complementary to a different allele at a locus, e.g., a bi-allelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligonucleotides can be used to specifically amplify, e.g., by PCR, or detect, a 26443 or 46873 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 26443 or 46873 gene.

Use of 26443 or 46873 Molecules as Surrogate Markers

The 26443 or 46873 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 26443 or 46873 molecules of the invention may be detected, and may be correlated with one or more biological states in vivo. For example, the 26443 or 46873 molecules of the invention may serve as surrogate markers for one or more disorders or disease states or for conditions leading up to disease states. As used herein, a "surrogate marker" is an objective biochemical marker that correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder.

Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 26443 or 46873 molecules of the invention are also useful as pharmacodynamic markers. As used herein, a "pharmacodynamic marker" is an objective biochemical marker that correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 26443 or 46873 marker) transcription or expression, the amplified marker may be in a quantity that is more readily detectable than the drug itself. Also, the marker may be more easily detected due to the nature of the marker itself; for example, using the methods described herein, anti-26443 or -46873 antibodies may be employed in an immune-based detection system for a 26443 or 46873 protein marker, or 26443- or 46873-specific radiolabeled probes may be used to detect a 26443 or 46873 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am, J. Health-Syst. Pharm.* 56 Suppl. 3: S16–S20.

The 26443 or 46873 molecules of the invention are also useful as pharmacogenomic markers. As used herein, a "pharmacogenomic marker" is an objective biochemical marker that correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 26443 or 46873 protein or RNA) for specific tumor markers in a subject, a drug or course of treatment may be selected that is optimized for the treatment of the specific tumor likely to be present in the subject. Similarly, the presence or absence of a specific sequence mutation in 26443 or 46873 DNA may correlate 26443 or 46873 drug response. The use of pharmacogenomic markers therefore permits the application of the most appropriate treatment for each subject without having to administer the therapy.

Pharmaceutical Compositions of 26443 and 46873

The nucleic acid and polypeptides, fragments thereof, as well as anti-26443 or 46873 antibodies (also referred to herein as "active compounds") of the invention can be incorporated into pharmaceutical compositions. Such compositions typically include the nucleic acid molecule, protein, or antibody and a pharmaceutically acceptable carrier. As used herein, the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including an agent in the composition that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indeces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The present invention encompasses agents that modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, although the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate, as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 26443 and 46873

The present invention provides for both prophylactic and therapeutic methods of treating a subject at risk of (or susceptible to) a disorder or having a disorder associated with aberrant or unwanted 26443 or 46873 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 26443 or 46873 molecules of the present invention or 26443 or 46873 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 26443 or 46873 expression or activity, by administering to the subject a 26443 or 46873 or an agent which modulates 26443 or 46873 expression or at least one 26443 or 46873 activity. Subjects at risk for a disease that is caused or contributed to by aberrant or unwanted 26443 or 46873 expression or activity can be identified by, for example, any or a combination of diagnostic or prognostic assays as described herein. Administration of a prophylactic agent can occur prior to the manifestation of symptoms characteristic of the 26443 or 46873 aberrance, such that a disease or disorder is prevented or, alternatively, delayed in its progression. Depending on the type of 26443 or 46873 aberrance, for example, a 26443 or 46873, 26443 or 46873 agonist or 26443 or 46873 antagonist agent can be used for treating the subject. The appropriate agent can be determined based on screening assays described herein.

It is possible that some 26443 or 46873 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of 26443 or 46873 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 26443 or 46873 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 26443 or 46873 expression is through the use of aptamer molecules specific for 26443 or 46873 protein. Aptamers are nucleic acid molecules having a tertiary structure that permits them to specifically bind to protein ligands (see, e.g., Osborne, et al. *Curr. Opin. Chem Biol.* 1997, 1(1): 5–9; and Patel, D. J. *Curr Opin Chem Biol June* 1997;1(1):32–46). Since nucleic acid molecules may in many cases be more conveniently introduced into target cells than therapeutic protein molecules may be, aptamers offer a method by which 26443 or 46873 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 26443 or 46873 disorders. For a description of antibodies, see the Antibody section above.

In circumstances wherein injection of an animal or a human subject with a 26443 or 46873 protein or epitope for stimulating antibody production is harmful to the subject, it is possible to generate an immune response against 26443 or 46873 through the use of anti-idiotypic antibodies (see, for example, Herlyn, D. *Ann Med* 1999;31(1):66–78; and Bhattacharya-Chatterjee, M., and Foon, K. A. *Cancer Treat Res* 1998;94:51–68). If an anti-idiotypic antibody is introduced into a mammal or human subject, it should stimulate the production of anti-anti-idiotypic antibodies, which should be specific to the 26443 or 46873 protein. Vaccines directed to a disease characterized by 26443 or 46873 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al., 1993, Proc. Natl. Acad. Sci. USA 90:7889–7893).

The identified compounds that inhibit target gene expression, synthesis and/or activity can be administered to a patient at therapeutically effective doses to prevent, treat or ameliorate 26443 or 46873 disorders. A therapeutically effective dose refers to that amount of the compound sufficient to result in amelioration of symptoms of the disorders.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 26443 or 46873 activity is used as a template, or "imprinting molecule", to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. A detailed review of this technique can be seen in Ansell, R. J. et al (1996) *Current Opinion in Biotechnology* 7:89–94 and in Shea, K. J. (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645–647. Through the use of isotope-labeling, the "free" concentration of compound which modulates the expression or activity of 26443 or 46873 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al (1995) *Analytical Chemistry* 67:2142–2144.

Another aspect of the invention pertains to methods of modulating 26443 or 46873 expression or activity for therapeutic purposes. Accordingly, in an exemplary embodiment, the modulatory method of the invention involves contacting a cell with a 26443 or 46873 or agent that modulates one or more of the activities of 26443 or 46873 protein activity associated with the cell. An agent that modulates 26443 or 46873 protein activity can be an agent as described herein, such as a nucleic acid or a protein, a naturally-occurring target molecule of a 26443 or 46873 protein (e.g., a 26443 or 46873 substrate or receptor), a 26443 or 46873 antibody, a 26443 or 46873 agonist or antagonist, a peptidomimetic of a 26443 or 46873 agonist or antagonist, or other small molecule.

In one embodiment, the agent stimulates one or 26443 or 46873 activities. Examples of such stimulatory agents include active 26443 or 46873 protein and a nucleic acid molecule encoding 26443 or 46873. In another embodiment, the agent inhibits one or more 26443 or 46873 activities. Examples of such inhibitory agents include antisense 26443 or 46873 nucleic acid molecules, anti26443 or 46873 antibodies, and 26443 or 46873 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 26443 or 46873 protein or nucleic acid molecule. In one embodiment, the method involves administering an agent (e.g., an agent identified by a screening assay described herein), or combination of agents that modulates (e.g., upregulates or downregulates) 26443 or 46873 expression or activity. In another embodiment, the method involves administering a 26443 or 46873 protein or nucleic acid molecule as therapy to compensate for reduced, aberrant, or unwanted 26443 or 46873 expression or activity.

Stimulation of 26443 or 46873 activity is desirable in situations in which 26443 or 46873 is abnormally downregulated and/or in which increased 26443 or 46873 activity is likely to have a beneficial effect. For example, stimulation of 26443 or 46873 activity is desirable in situations in which a 26443 or 46873 is downregulated and/or in which increased 26443 or 46873 activity is likely to have a beneficial effect. Likewise, inhibition of 26443 or 46873 activity is desirable in situations in which 26443 or 46873 is abnormally upregulated and/or in which decreased 26443 or 46873 activity is likely to have a beneficial effect.

Examples of other disorders which can be treated include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

In addition, aberrant activity of a 26443 or 46873 polypeptide may adversely affect a muscle cell. Examples of disorders involving, for example, heart muscle, or "cardiovascular disorders", include, but are not limited to, a disease, disorder, or state involving the cardiovascular system, e.g., the heart, and or coronary blood vessels. A cardiovascular disorder can be caused by a malfunction of the heart, an imbalance in arterial pressure or an occlusion of a blood vessel, e.g., by a thrombus. Examples of such disorders include arrhythmias, myocardial infarction, hypertension, athlerosclerosis, coronary artery spasm, congestive heart failure, coronary artery disease, valvular disease and cardiomyopathies. Additionally, skeletal muscle cells may be affected by aberrant activity of a 26443 or 46873 polypeptide. For instance, symptoms of a skeletal muscular disorder may include aching muscles, muscle cramps or muscle degeneracy.

Examples of liver disorders include, but are not limited to, disorders associated with an accumulation of fibrous tissue, such as that resulting from an imbalance between production and degradation of the extracellular matrix accompanied by the collapse and condensation of preexisting fibers; hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic); hepatic injury, such as portal hypertension or hepatic fibrosis; liver fibrosis attributed to inborn errors of metabolism, for example, fibrosis resulting from a storage disorder such as Gaucher's disease (lipid abnormalities) or a glycogen storage disease, e.g., A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome); liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder, such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 26443 or 46873 may play an important role in overall metabolism. Diseases of metabolic imbalance include, but are not limited to, obesity, anorexia nervosa, cachexia and lipid disorders diabetes.

Moreover, a 26443 or 46873 protein may regulate cellular amino acid levels (e.g., asparagine, aspartic acid). A defect or deficiency in a 26443 or 46873 polypeptide, therefore, may result in inappropriate levels of, e.g., asparagine and/or aspartic acid, thereby causing a variety of disorders, for example, neurological disorders. Examples of neural disorders include, but are not limited to, neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease; psychiatric disorders, e.g., depression, schizophrenic disorders, Korsakoff's psychosis, mania, anxiety disorders, or phobic disorders; learning or memory disorders, e.g., amnesia or age-related memory loss; and neurological disorders, e.g., migraine. The ability to regulate or control the expression of a 26443 or 46873 protein may result in the ability to likewise regulate or control levels of amino acids, e.g., asparagine or aspartic acid, thereby providing a protective and/or therapeutic effect against, e.g., neurological disorders.

Thus, the 26443 or 46873 molecules can act as novel diagnostic targets and therapeutic agents for controlling defects resulting in metabolic deficiencies and/or improper amino acid levels, e.g., asparagine or aspartic acid.

Aberrant expression and/or activity of 26443 or 46873 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 26443 or 46873 molecules effects in bone cells, e.g., osteoclasts and osteoblasts, that may in turn result in bone formation and degeneration. For example, 26443 or 46873 molecules may support different activities of bone resorbing osteoclasts, such as the stimulation of differentiation of monocytes and mononuclear phagocytes into osteoclasts. Accordingly, 26443 or 46873 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Additionally, 26443 or 46873 molecules may play an important role in the etiology of certain viral diseases, including but not limited to Hepatitis B, Heptitis C and Herpes Simplex Virus (HSV). Modulators of 26443 or 46873 activity could be used to control viral diseases. The modulators can be used in the treatment and/or diagnosis of viral infected tissue or virus-associated tissue fibrosis, especially liver and liver fibrosis. Also, 26443 or 46873 modulators can be used in the treatment and/or diagnosis of virus-associated carcinoma, especially hepatocellular cancer and lymphomas.

Additionally, 26443 or 46873 may play an important role in the regulation of pain disorders. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York:McGraw-Hill); pain associated with musculoskeletal disorders, e.g., joint pain; tooth pain; headaches; pain associated with surgery; pain related to irritable bowel syndrome; or chest pain.

26443 and 46873 Pharmacogenomics

The 26443 or 46873 molecules of the present invention, as well as agents, or modulators which have a stimulatory or inhibitory effect on 26443 or 46873 activity (e.g., 26443 or 46873 gene expression) as identified by a screening assay described herein can be administered to individuals to treat (prophylactically or therapeutically) 26443 or 46873 associated disorders (e.g., metabolic disorders or defects associated with fatty acid oxidation) associated with aberrant or unwanted 26443 or 46873 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 26443 or 46873 molecule or 26443 or 46873 modulator as well as tailoring the dosage and/or therapeutic regimen of treatment with a 26443 or 46873 molecule or 26443 or 46873 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11):983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 26443 or 46873 protein of the present invention), all common variants of that gene can be fairly easily identified in the population and it can be determined if having one version of the gene versus another is associated with a particular drug response.

Alternatively, a method termed "gene expression profiling" can be utilized to identify genes that predict drug response. For example, the gene expression of an animal dosed with a drug (e.g., a 26443 or 46873 molecule or 26443 or 46873 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 26443 or 46873 molecule or 26443 or 46873 modulator, such as a modulator identified by one of the exemplary screening assays described herein.

The present invention further provides methods for identifying new agents, or combinations, that are based on identifying agents that modulate the activity of one or more of the gene products encoded by one or more of the 26443 or 46873 genes of the present invention, wherein these products may be associated with resistance of the cells to a therapeutic agent. Specifically, the activity of the proteins encoded by the 26443 or 46873 genes of the present invention can be used as a basis for identifying agents for overcoming agent resistance. By blocking the activity of one or more of the resistance proteins, target cells will become sensitive to treatment with an agent that the unmodified target cells were resistant to.

Monitoring the influence of agents (e.g., drugs) on the expression or activity of a 26443 or 46873 protein can be applied in clinical trials. For example, the effectiveness of an agent determined by a screening assay as described herein to increase 26443 or 46873 gene expression, protein levels, or upregulate 26443 or 46873 activity, can be monitored in clinical trials of subjects exhibiting decreased 26443 or 46873 gene expression, protein levels, or downregulated 26443 or 46873 activity. Alternatively, the effectiveness of an agent determined by a screening assay to decrease 26443 or 46873 gene expression, protein levels, or downregulate 26443 or 46873 activity, can be monitored in clinical trials of subjects exhibiting increased 26443 or 46873 gene expression, protein levels, or upregulated 26443 or 46873 activity. In such clinical trials, the expression or activity of a 26443 or 46873 gene, and preferably, other genes that have been implicated in, for example, a 26443- or 46873-associated disorder can be used as a "read out" or markers of the phenotype of a particular cell.

26443 or 46873 Informatics

The sequence of a 26443 or 46873 molecule is provided in a variety of media to facilitate use thereof. A sequence can be provided as a manufacture, other than an isolated nucleic acid or amino acid molecule, which contains a 26443 or 46873. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 26443 or 46873 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention that match a particular target sequence or target motif. The search can be a BLAST search or other routine sequence comparison, e.g., a search described herein.

Thus, in one aspect, the invention features a method of analyzing 26443 or 46873, e.g., analyzing structure, function, or relatedness to one or more other nucleic acid or amino acid sequences. The method includes: providing a 26443 or 46873 nucleic acid or amino acid sequence; comparing the 26443 or 46873 sequence with a second sequence, e.g., one or more preferably a plurality of sequences from a collection of sequences, e.g., a nucleic acid or protein sequence database to thereby analyze 26443 or 46873. The method can be performed in a machine, e.g., a computer, or manually by a skilled artisan.

The method can include evaluating the sequence identity between a 26443 or 46873 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 26443 or 46873 sequence that includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 26443 or 46873 sequence, or record, in machine-readable form; comparing a second sequence to the 26443 or 46873 sequence; thereby analyzing a sequence. Comparison can include comparing to sequences for sequence identity or determining if one sequence is included within the other, e.g., determining if the 26443 or 46873 sequence includes a sequence being compared. In a preferred embodiment the 26443 or 46873 or second sequence is stored on a first computer, e.g., at a first site and the comparison is performed, read, or recorded on a second computer, e.g., at a second site. E.g., the 26443 or 46873 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 26443- or 46873-associated disease or disorder or a pre-disposition to a 26443- or 46873-associated disease or disorder, wherein the method comprises the steps of determining 26443 or 46873 sequence information associated with the subject and based on the 26443 or 46873 sequence information, determining whether the subject has a 26443- or 46873-associated disease or disorder or a pre-disposition to a 26443- or 46873-associated disease or disorder and/or recommending a particular treatment for the disease, disorder or pre-disease condition.

The invention further provides in an electronic system and/or in a network, a method for determining whether a subject has a 26443- or 46873-associated disease or disorder or a pre-disposition to a disease associated with a 26443 or 46873 wherein the method comprises the steps of determining 26443 or 46873 sequence information associated with the subject, and based on the 26443 or 46873 sequence information, determining whether the subject has a 26443- or 46873-associated disease or disorder or a pre-disposition to a 26443- or 46873-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 26443 or 46873 sequence of the subject to the 26443 or 46873 sequences in the database to thereby determine whether the subject as a 26443- or 46873-associated disease or disorder, or a pre-disposition for such.

The present invention also provides in a network, a method for determining whether a subject has a 26443- or 46873-associated disease or disorder or a pre-disposition to a 26443- or 46873-associated disease or disorder associated with 26443 or 46873, said method comprising the steps of receiving 26443 or 46873 sequence information from the subject and/or information related thereto, receiving phenotypic information associated with the subject, acquiring information from the network corresponding to 26443 or 46873 and/or corresponding to a 26443- or 46873-associated disease or disorder (e.g., a disorder associated with aberrant or unwanted 26443 or 46873 expression or activity), and based on one or more of the phenotypic information, the 26443 or 46873 information (e.g., sequence information and/or information related thereto), and the acquired information, determining whether the subject has a 26443- or 46873-associated disease or disorder or a pre-disposition to a 26443- or 46873-associated disease or disorder. The method may further comprise the step of recommending a particular treatment for the disease, disorder or pre-disease condition.

The present invention also provides a method for determining whether a subject has a 26443- or 46873-associated disease or disorder or a pre-disposition to a 26443- or 46873-associated disease or disorder, said method comprising the steps of receiving information related to 26443 or 46873 (e.g., sequence information and/or information related thereto), receiving phenotypic information associated with the subject, acquiring information from the network related to 26443 or 46873 and/or related to a 26443- or 46873-associated disease or disorder, and based on one or more of the phenotypic information, the 26443 or 46873 information, and the acquired information, determining whether the subject has a 26443- or 46873-associated disease or disorder or a pre-disposition to a 26443- or 46873-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

EXAMPLES

Examples for 26443 and 46873

Example 1

Identification and Characterization of Human 26443 or 46873 cDNA

The human 26443 sequence (FIG. 1; SEQ ID NO: 1), which is approximately 1888 nucleotides long, including 5' and 3'untranslated regions, contains a predicted methionine-initiated coding sequence of about 1254 nucleotides (SEQ ID NO:3 and nucleotides 91 to 1344 of SEQ ID NO: 1). The coding sequence encodes an 418 amino acid protein (SEQ ID NO:2).

The human 46873 sequence (FIG. 5; SEQ ID NO:4), which is approximately 1358 nucleotides long, including 5' and 3'untranslated regions, contains a predicted methionine-initiated coding sequence of about 924 nucleotides (SEQ ID NO:3 and nucleotides 134 to 1057 of SEQ ID NO: 1). The coding sequence encodes an 308 amino acid protein (SEQ ID NO:2).

Example 2

Tissue Distribution of 26443 or 46873 mRNA by Large-Scale Tissue-Specific Library Sequencing and by Northern Blot Hybridization Northern blot hybridizations with various RNA samples can be performed under standard conditions and washed under stringent conditions, i.e., 0.2×SSC at 65° C. A DNA probe corresponding to all or a portion of the 26443 or 46873 cDNA (SEQ ID NO: 1 or SEQ ID NO:4, respectively) can be used. The DNA was radioactively labeled with $^{32}$P-dCTP using the Prime-It Kit (Stratagene, La Jolla, Calif.) according to the instructions of the supplier. Filters containing mRNA from mouse liver, hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 3

Recombinant Expression of 26443 or 46873 in Bacterial Cells

In this example, 26443 or 46873 is expressed as a recombinant glutathione-S-transferase (GST) fusion polypeptide in *E. coli* and the fusion polypeptide is isolated and characterized. Specifically, 26443 or 46873 is fused to GST and this fusion polypeptide is expressed in *E. coli*, e.g., strain PEB199. Expression of the GST-26443 or -46873 fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 26443 or 46873 Protein in COS Cells

To express the 26443 or 46873 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 26443 or 46873 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 26443 or 46873 DNA sequence is amplified by PCR using two primers. The 5' primer contains the restriction site of interest followed by approximately twenty nucleotides of the 26443 or 46873 coding sequence starting from the initiation codon; the 3' end sequence contains complementary sequences to the other restriction site of interest, a translation stop codon, the HA tag or FLAG tag and the last 20 nucleotides of the 26443 or 46873 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably, the two restriction sites chosen are different so that the 26443 or 46873 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 26443- or 46873-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the 26443 or 46873 polypeptide is detected by radiolabeling ($^{35}$S-methionine or $^{35}$S-cysteine, available from NEN, Boston, Mass., can be used) and immunoprecipitation (Harlow, E. and Lane, D. *Antibodies: A Laboratory Manual,* Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 26443 or 46873 coding sequence is cloned directly into the polylinker of the pcDNA/Amp vector using the appropriate restriction sites. The resulting plasmid is transfected into COS cells in the manner described above, and the expression of the 26443 or 46873 polypeptide is detected by radiolabeling and immunoprecipitation using a 26443 or 46873 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising the nucleic acid sequence of SEQ ID NO:4 or a full complement thereof.

2. An isolated nucleic acid molecule consisting of the nucleic acid sequence of SEQ ID NO:4 or SEQ ID NO:6, or a full complement thereof.

3. The nucleic acid molecule of claim 1, further comprising vector nucleic acid sequences.

4. The nucleic acid molecule of claim 2, further comprising vector nucleic acid sequences.

5. The nucleic acid molecule of claim 1, further comprising nucleic acid sequences encoding a heterologous polypeptide.

6. The nucleic acid molecule of claim 2, further comprising nucleic acid sequences encoding a heterologous polypeptide.

7. An isolated host cell which contains the nucleic acid molecule of claim 3.

8. The host cell of claim 7 which is a mammalian host cell.

9. An isolated host cell which contains the nucleic acid molecule of claim 4.

10. The host cell of claim 9 which is a mammalian host cell.

11. A method for producing a polypeptide, comprising culturing the host cell of claim 7 under conditions in which the polypeptide encoded by the nucleic acid molecule is expressed.

12. A method for producing a polypeptide, comprising culturing the host cell of claim 9 under conditions in which the polypeptide encoded by the nucleic acid molecule is expressed.

* * * * *